United States Patent [19]
Lippton

[11] Patent Number: 5,840,696
[45] Date of Patent: Nov. 24, 1998

[54] DIURETIC AND ANTINATRIURETIC RESPONSES PRODUCED BY THE ENDOGENOUS OPIOID-LIKE PEPTIDE, NOCICEPTIN (ORPHANIN FQ)

[76] Inventor: Howard Lippton, 144 Elks Pl., Suite 1602, New Orleans, La. 70112

[21] Appl. No.: 927,328

[22] Filed: Sep. 11, 1997

[51] Int. Cl.[6] .......................... A61K 38/00; A61K 38/10; C07K 7/00
[52] U.S. Cl. .................................. 514/13; 514/2; 530/326
[58] Field of Search ................................ 514/13; 530/326

[56] References Cited

PUBLICATIONS

Meunier, J.C. et al., Nature, 377, 532, Feb. 1995.
Reinscheid, R.K. et al, Science, 270, 792, Mar. 1995.
Giuliani, S. et al. British J. Pharmacol., 118 (7) 1567, Jul. 1996.
Kapusta D. et al. Life Sci. 60 (1) PL15–PL21 Jan. 1997.

*Primary Examiner*—Cecilia J. Tsang
*Assistant Examiner*—Michael Borin
*Attorney, Agent, or Firm*—Pravel, Hewitt, Kimball & Krieger

[57] ABSTRACT

Nociceptin in a method of controlling water retention in a patient. More particularly, the use and administration of nociceptin as a free-water diuretic that produces a free-water diuresis for the control of water retention in patients.

10 Claims, 23 Drawing Sheets

Figure 1:

Amino acid sequences of nociceptin and dynorphin A. Identical amino acids are italicized.

nociceptin:

Phe-*Gly-Gly-Phe*-Thr-Gly-Ala-Arg-Lys-Ser-Ala-Arg-*Lys*-Leu-Ala-*Asn-Gln* dynorphin A:

Tyr-*Gly-Gly-Phe*-Leu-Arg-Arg-Ile-Arg-Pro-Lys-Leu-*Lys*-Trp-Asp-*Asn-Gln*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: SINGLE
        ( D ) TOPOLOGY: linear ( i i ) MOLECULE TYPE: Peptide ( x i ) SEQUENCE DESCRIPTION: SEQ ID NO:1:

```
Phe  Gly  Gly  Phe  Thr  Gly  Ala  Arg  Lys  Ser
1                   5                        10
Ala  Arg  Lys  Leu  Ala  Asn  Gln
                    15
```

( 2 ) INFORMATION FOR SEQ ID NO:2:

( i ) SEQUENCE CHARACTERISTICS:
        ( A ) LENGTH: 17 amino acids
        ( B ) TYPE: amino acids
        ( C ) STRANDEDNESS: SINGLE
        ( D ) TOPOLOGY: linear ( i i ) MOLECULE TYPE: Peptide ( x i ) SEQUENCE DESCRIPTION: SEQ ID NO:2:

```
Tyr  Gly  Gly  Phe  Leu  Arg  Arg  Ile  Arg  Pro
1                   5                        10
Lys  Leu  Lys  Trp  Asp  Asn  Gln
                    15
```

DIURETIC AND ANTINATRIURETIC RESPONSES PRODUCED BY THE ENDOGENOUS OPIOID-LIKE PEPTIDE, NOCICEPTIN (ORPHANIN FQ)

STATEMENT REGARDING FEDERALLY SPONSORED RESEARCH

This research may have been partially funded by a United States federal grant from the National Institute of Diabetes and Digestive and Kidney Diseases grant DK-43337. The United States Government may, therefore, have certain rights to this invention.

CROSS-REFERENCE TO RELATED APPLICATIONS

This application claims the benefit of United States Provisional Patent Application No. 06/026,000 filed Sep. 12, 1996 by Daniel R. Kapusta and Howard Lippton, and entitled Diuretic and Antinatriuretic Responses Produced by the Endogenous Opioid-Like Peptide, Nociceptin (Orphanin FQ), which is hereby incorporated by reference in its entirety.

BACKGROUND OF THE INVENTION

1. Field of the Invention

The present invention relates to a method of controlling water retention in a patient. More particularly, the present invention relates to the use and administration of a free-water diuretic that produces a free-water diuresis. Still more particularly, the present invention relates to the administration and use of nociceptin (Orphanin FQ) as a free-water diuretic for the control of water retention in patients.

2. General Background

Water diuretics (also known as solute free-water diuretics, or aquaretics) are required for the management of hyponatremic states such as the syndrome of inappropriate secretion of antidiuretic hormone (SIADH) or other potentially life-threatening water-retaining diseases including congestive heart failure, renal failure, liver cirrhosis with ascites, or adult respiratory distress syndrome (ARDS). Since the primary control of water homeostasis involves vasopressin (antidiuretic hormone, ADH), the development of water diuretics has been directed toward 1) inhibiting the action of vasopressin at the level of the kidneys using vasopressin V2 receptor antagonists or 2) inhibiting the secretion of vasopressin from the hypothalamus using kappa opioid agonists. Despite considerable research efforts, the development of free water diuretics by these approaches has been complicated and unsuccessful. In this regard, vasopressin antagonists have been shown to have limited potential as diuretics due to their partial agonist and species-dependent properties. In contrast, whereas kappa opioid agonists elicit a profound water diuresis in man, their clinical use is prevented by the central nervous system side effects (i.e. dysphoria) produced by this class of opioids. Thus, currently there are no free water diuretics available for clinical use in the U.S. or other countries.

SUMMARY OF THE INVENTION:

The technology of the present invention is the clinical use of nociceptin, a novel opioid-like peptide, as a selective water diuretic. The present invention relates to the clinical use of nociceptin as a water diuretic for the management of hyponatremic and water-retaining diseases.

In an embodiment of the practice of the method of the present invention, nociceptin is used as a water diuretic for the chronic prophylactic management of hyponatremia and/or water-retention in out-patients with the syndrome of inappropriate secretion of antidiuretic hormone (SIADH), congestive heart failure or cirrhosis with ascites. The agent of the instant invention is particularly useful for the acute removal of fluid in certain states of congestive heart failure or in the adult respiratory distress syndrome in which water retention may be life-threatening. The present invention may also be used for, including but not limited to, congestive heart failure, liver cirrhosis with ascites, renal failure (acute and chronic), nephrotic syndrome, edematous states of the lung, non-cardiogenic pulmonary edema, near drowning, adult respiratory distress syndrome (ARDS), neurogenic pulmonary edema, pleural effusions, volume overload, electrolyte and acid base disorders including hyperatremia, pregnancy induced hyperolemia, syndrome of innappriate antidiuretic hormone (SIADH), drug-induced edema including drugs to treat hypertension and inflammation, refeeding edema, acute glomerulonephritis, and tumor-induced edema systemic in location including brain edema. The method of the present invention extends to the administration of nociceptin to all individuals with acute or chronic hyponatremic or water-retaining states.

Still further, since nociceptin produces a free-water diuresis via a central pathway that is independent of kappa-opioid receptors, this indicates that nociceptin is devoid of producing dysphoria, a kappa-opioid receptor mediated adverse effect.

In the fall of 1995, nociceptin (also known as Orphanin FQ), a novel peptide from brain tissue, was isolated and shown to have an amino acid sequence most similar to that of the endogenous opioid peptide dynorphin A (a kappa opioid agonist), FIG. 1. In preliminary studies in laboratory animals (e.g. rodents), we have demonstrated that intravenous infusion of nociceptin produces a profound increase in urine flow rate and decrease in urinary sodium excretion (i.e. a free-water diuresis). In further studies, intracerebroventricular (i.c.v.) microinjection of nociceptin into conscious rats also produced a concurrent diuresis and antinatriuresis.

The magnitude and pattern of the central nociceptin-induced water diuresis was similar to that produced by i.c.v. administration of the endogenous kappa-opioid agonist, dynorphin A. Whereas i.c.v. pre-treatment with the selective kappa-opioid receptor antagonist, nor-binaltorphimine, completely prevented the renal responses produced by dynorphin A, this antagonist did not alter the free-water diuresis produced by central nociceptin. Thus, the present invention shows that nociceptin produces a water diuresis qualitatively similar to that elicited by kappa-opioid agonists, but via a different physiological pathway.

Some advantages of the present invention are the ability of nociceptin to produce a selective water diuresis unique in that only two classes of drugs have been demonstrated to elicit such a response, these being vasopressin V2 antagonists, and kappa-opioid agonists. For reasons mentioned above, however, these two classes of drugs have not been successfully developed as water diuretics for use in humans. In particular, and not wishing to be tied to any specific model or pathway, we have demonstrated that the water diuresis produced by nociceptin is mediated by a central pathway that is independent of kappa-opioid receptors. This is of importance clinically since it is recognized that the dysphoria produced by kappa opioid agonists is mediated by activation of central kappa opioid receptors. Because of the ability of nociceptin to produce a selective water diuresis via a pathway that is independent of central kappa-opioid receptors, it is likely that these agents may be devoid of producing dysphoria, yet retain their therapeutic water diuretic properties. In this respect, nociceptin offers a clinically useful therapeutic tool for the management of edematous states, hyponatremia and water retaining diseases.

BRIEF DESCRIPTION OF THE DRAWINGS

FIG. 1 shows the amino acid sequence of nociceptin 1 and its alignment based on homology to dynorphin A;

FIG. 3 shows a dose-response study of the cardiovascular and renal responses produced by i.c.v. nociceptin administration in conscious Sprague-Dawley rats (see Example 2). The values are means±S.E. and illustrate the systemic cardiovascular and renal effects produced by i.c.v. administration of 1 µg (●; n=6), 10 µg (▼; n=6), or 30 µg (■; n=6) nociceptin per rat. The cardiovascular and renal responses produced by intravenous (i.v.) bolus administration of 30 µg nociceptin (□; n−6) are also shown. Urine samples were collected during control (C)(20 min) and 10 min after nociceptin injection for 60 min, denoted as time periods 20 to 70 min (consecutive 10 min samples). Abbreviations are HR, heart rate; MAP, mean arterial pressure; V, urine flow rate; and $U_{Na}V$, urinary sodium excretion. Statistical significance within each group was determined by a repeated measures analysis of variance followed by a Bonferroni multiple comparisons test; asterisks (a, b, or c) denote a significant change ($p<0.05$) from control within each group. The stability of cardiovascular and renal excretory parameters following i.c.v. injection of isotonic saline vehicle (5 µl) under similar experimental conditions has been previously demonstrated (7, 12).

Figure 3:
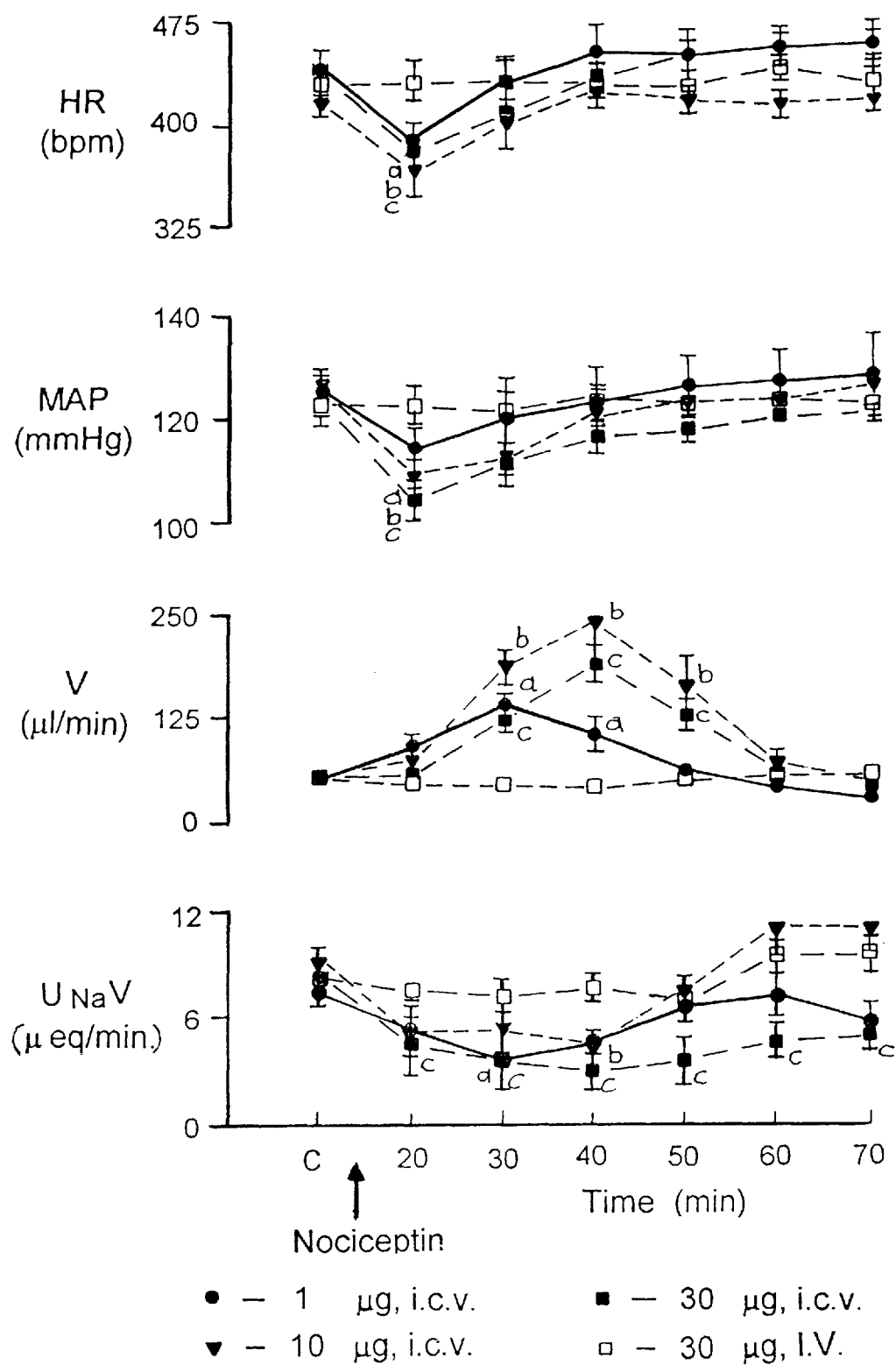
FIG. 3 illustrates the cardiovascular and renal responses produced by bolus intracerebroventricular (i.c.v.) administration of nociceptin and bolus intravenous (i.v.) administration of nociceptin. Specifically.

(A) The values are means±S.E. and illustrate the changes in urine flow rate (V) and urinary sodium excretion ($U_{Na}V$) produced by i.c.v. administration of 10 µg nociceptin (▼; n=6, data from FIG. 3 and superimposed in FIG. 4A) or dynorphin A (●;n=6) in naive rats (n=6 per group). Urine samples were collected during control (C) (20 min) and 10 min after nociceptin or dynorphin A injection for 60 min, denoted as time periods 20 to 70 min (consecutive 10 min samples).

The stability of cardiovascular and renal excretory parameters following i.c.v. injection of isotonic saline vehicle (5 µl) under similar experimental conditions has been previously demonstrated (7, 12).

(B) The values are means±S.E. and illustrate the renal excretory responses produced by i.c.v. administration of 10 µg nociceptin (∇; n=6) or dynorphin A (○; n=6) in rats pre-treated i.c.v. with nor-binaltorphimine (n=6 per group). Urine samples were collected during control (C) (20 min), 10 min after nor-binaltorphimine injection (N, 1 µg total i.c.v., 10 min sample) and for 60 min, starting 10 min after i.c.v. nociceptin or dynorphin A injection (consecutive 10 min samples). Abbreviations are V, urine flow rate and $U_{Na}V$, urinary sodium excretion.

Figure 5:
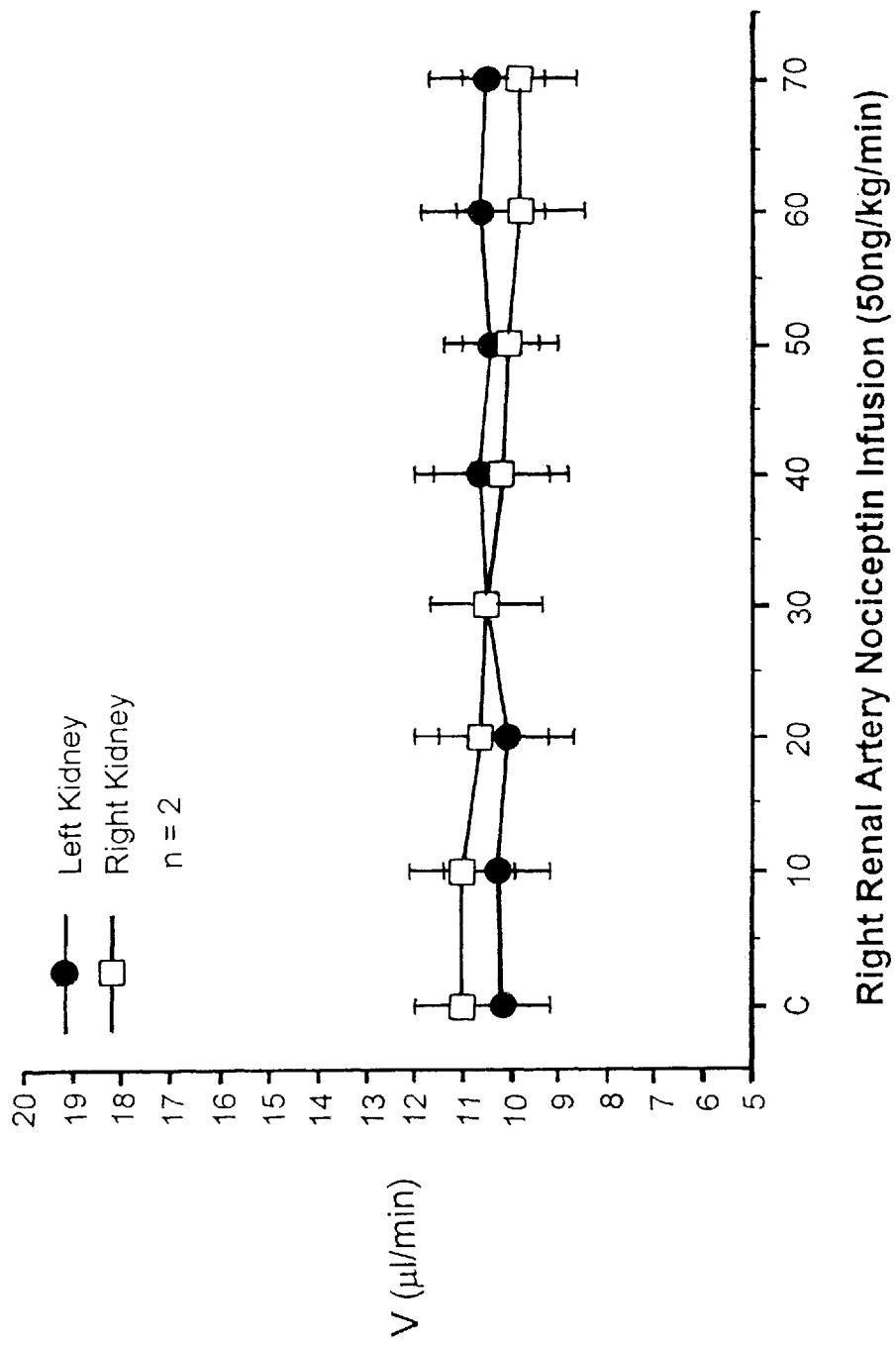

FIG. 5 compares the effects of nociceptin on left kidney urine flow rate (V) and right kidney urine flow rate (V) in the rat when infused into the right renal artery. N=number of animals.

Figure 6:
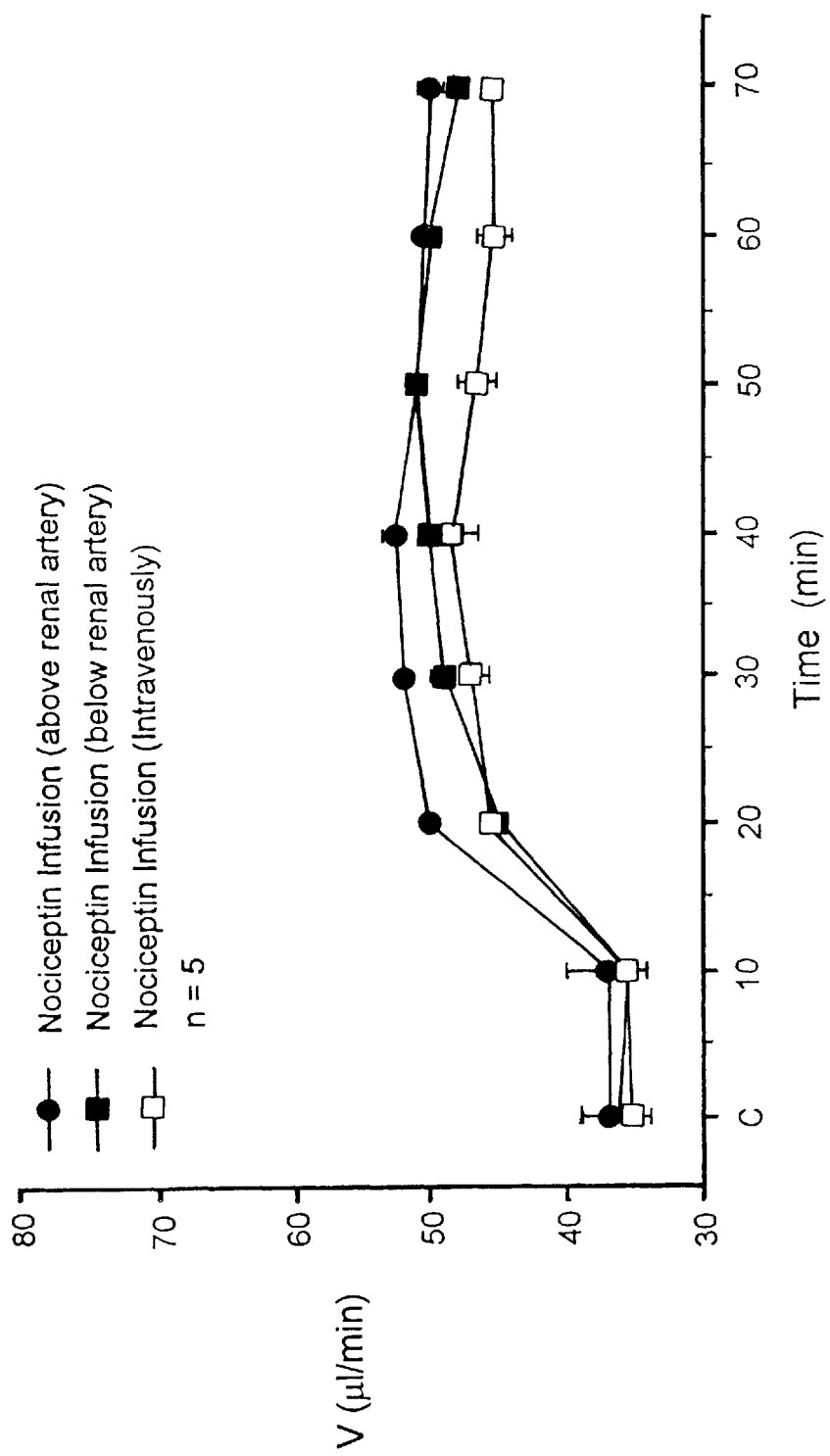

FIG. 6 compares the effects of three different sites of infusion: above renal artery in aorta, below renal artery in aorta, and intravenously on urine flow rate (V) in the conscious rat. N=number of rats. Aortic catheters were positioned flouroscopically. Nociceptin was infused at 50 nanog/kg/min for each infusion site.

Figure 7:
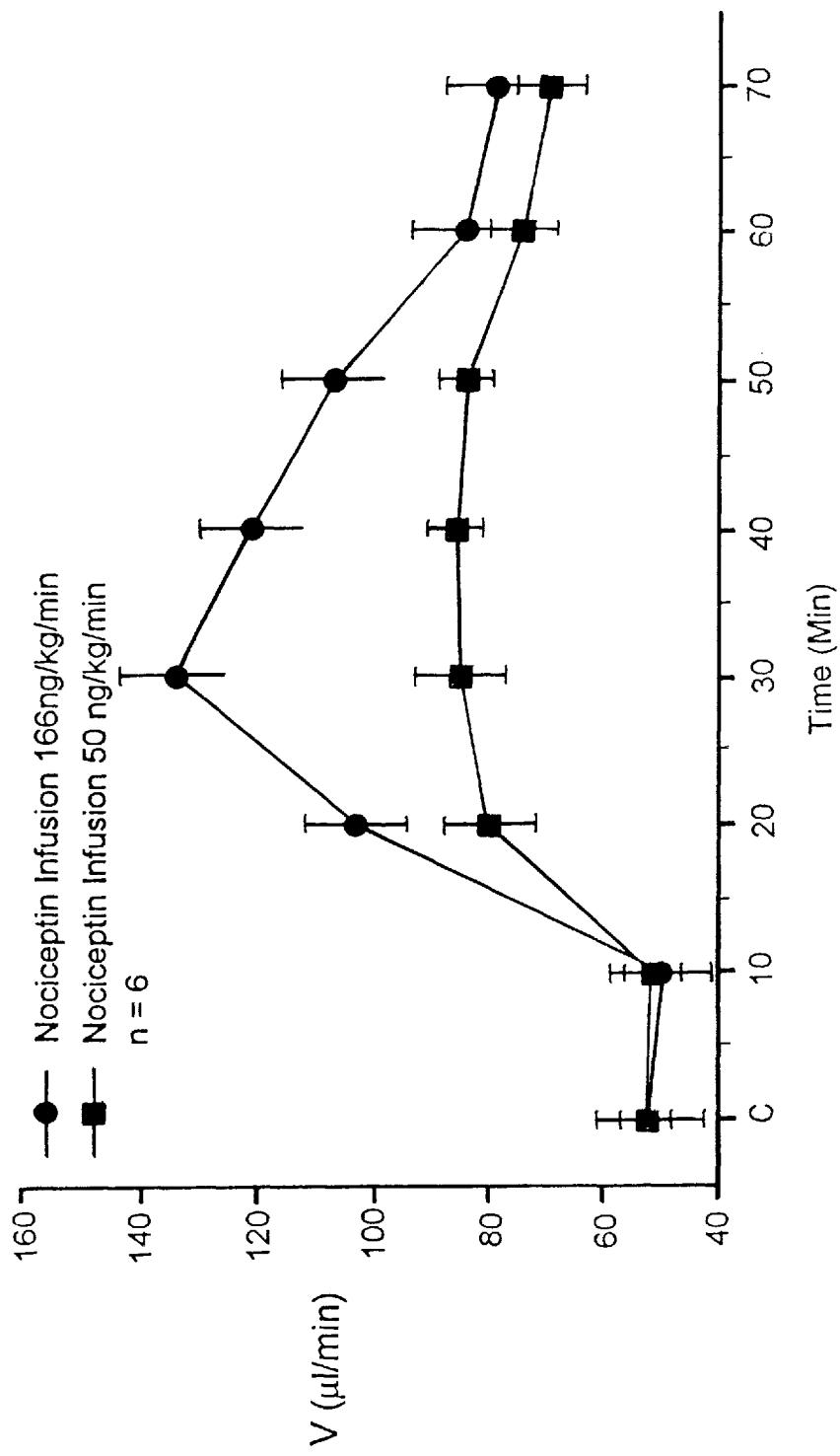

FIG. 7 illustrates the effects of intravenous (i.v.) infusion of nociceptin on the urine flow rate (V) of conscious rats.

Figure 8:
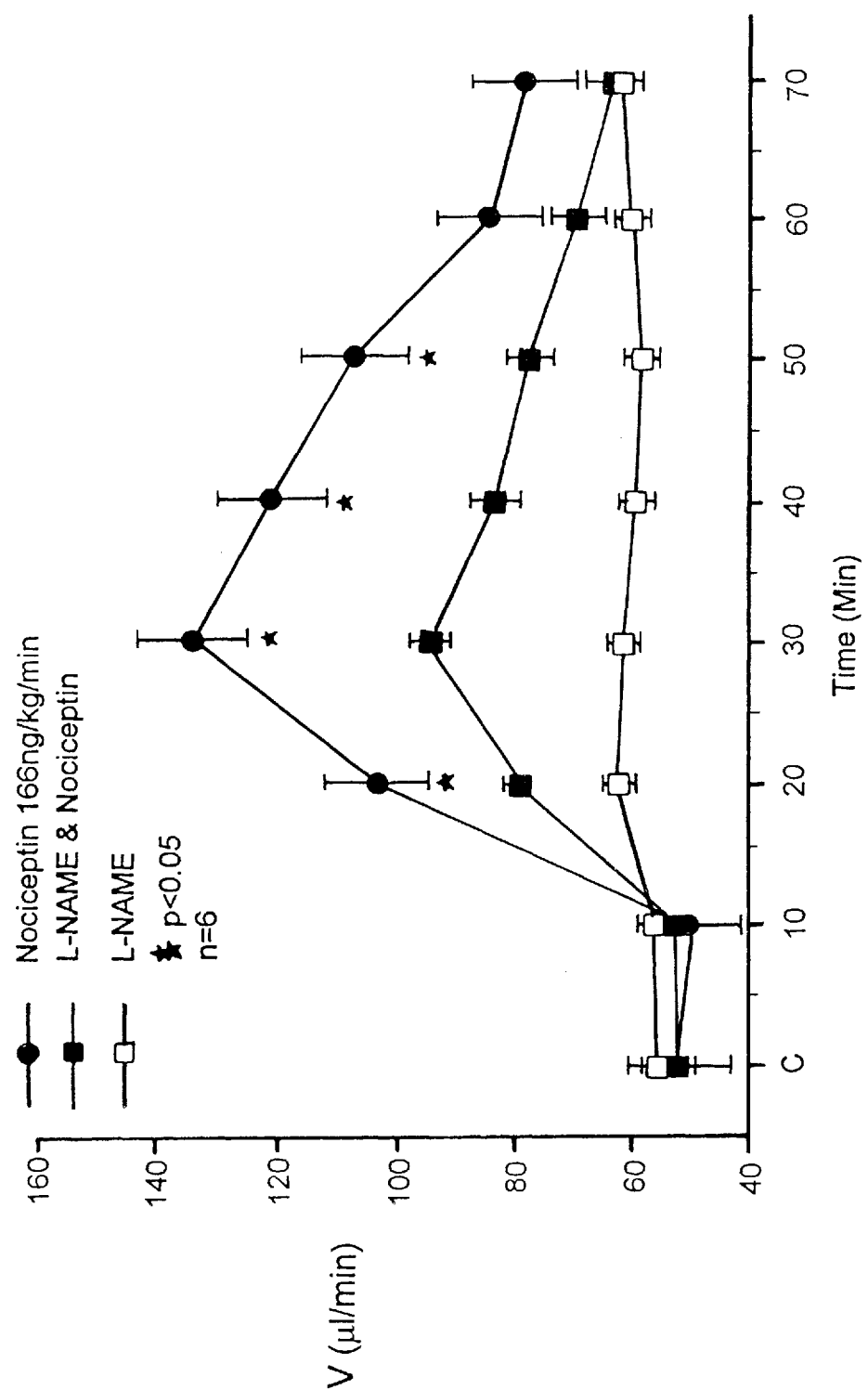

FIG. 8 shows inhibition of an increase in urine flow rate (V) in response to intravenous (i.v.) infusion of nociceptin into conscious rats before and after administration of L-nitro arginine methyl ester (L-NAME); an inhibitor of constituitive nitric oxide formation. The effects of L-NAME on baseline urine flow rate (V) of conscious rats are also illustrated in FIG. 6.

Figure 9:
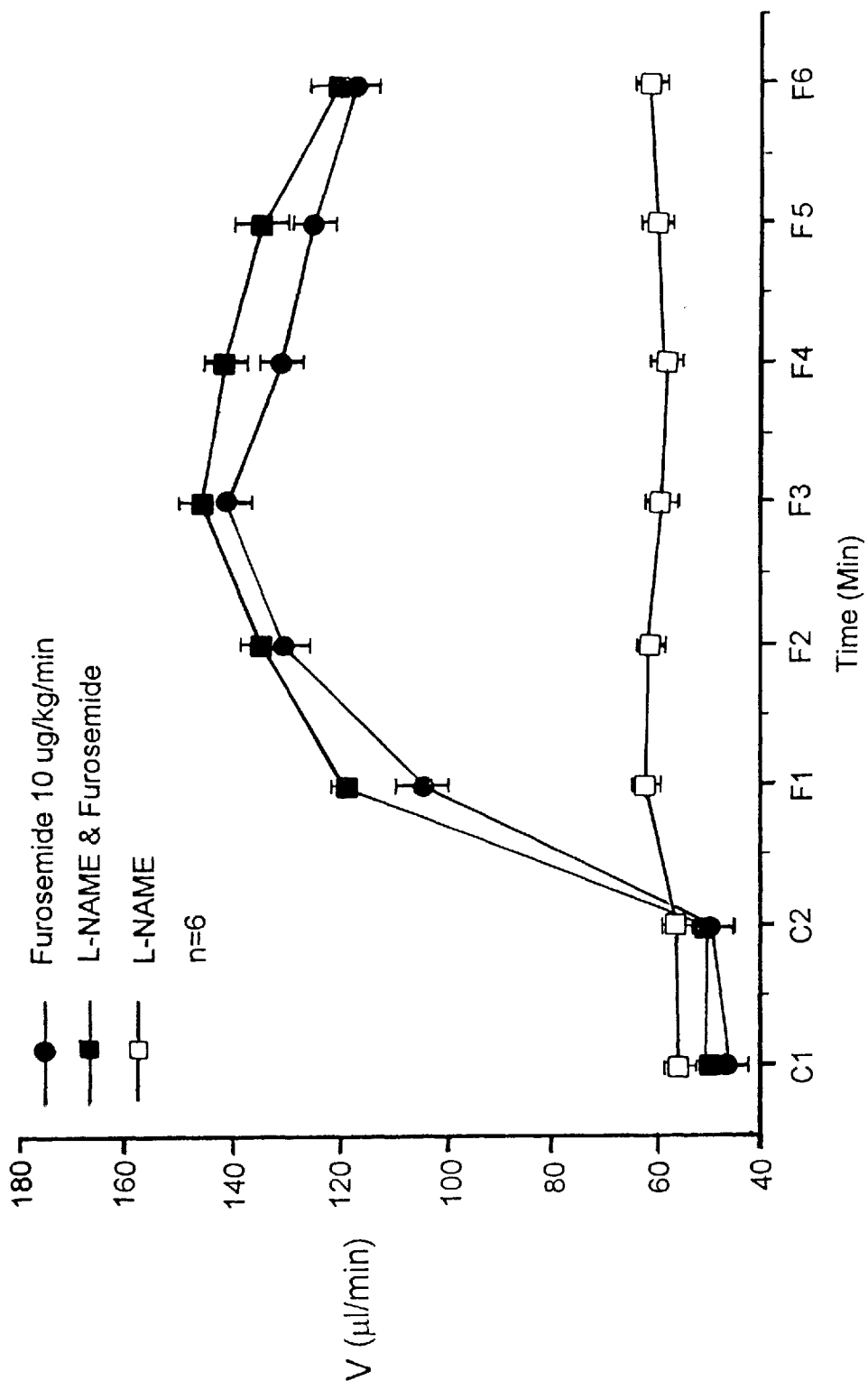

FIG. 9 illustrates the influence of L-nitro arginine methyl ester (L-NAME) on changes in urine flow rate (V) in response to furosemide. Furosemide (Lasix™) is a well-known, clinically used loop-diuretic that acts independently of nociceptin receptor activation.

Figure 10:
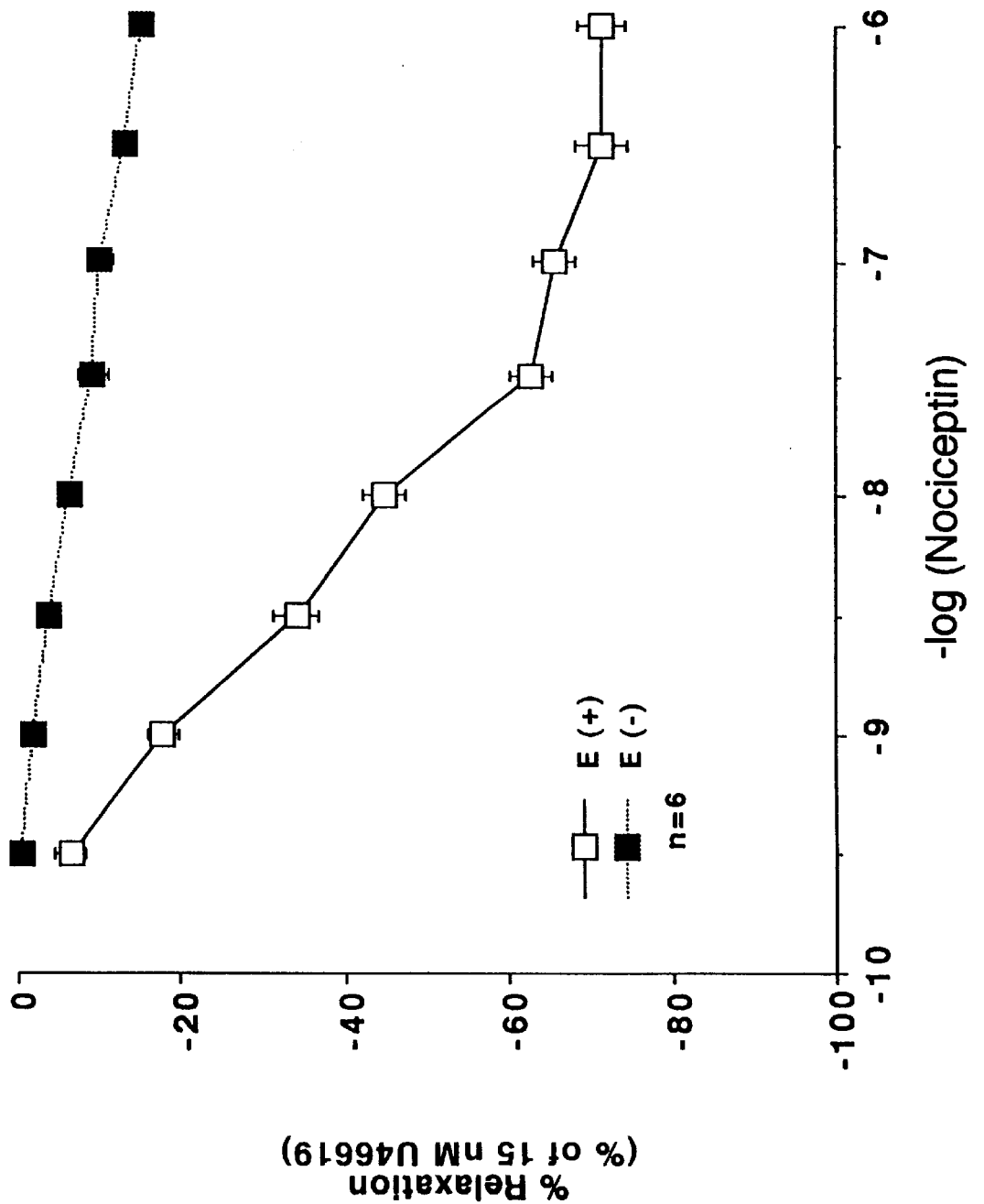

FIG. 10 illustrates the effects of nociceptin on isolated rat aortic vascular rings in vitro with an intact endothelial cell layer (E(+)) and following endothelial cell removal (E(−)). Aortic rings were precontracted with U46619, a thromboxane $A_2$ mimic.

Figure 11:
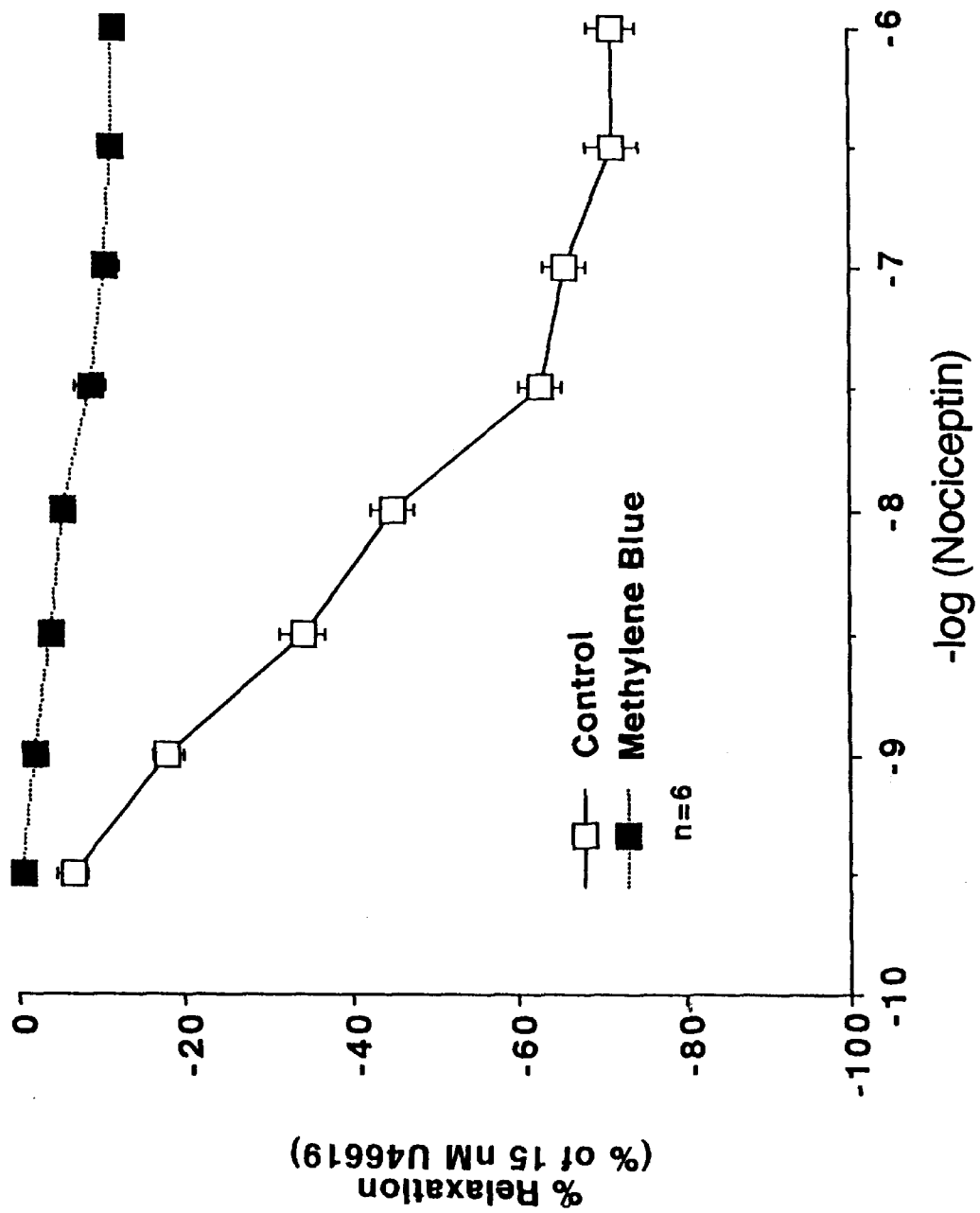

FIG. 11 illustrates that effects of methylene blue (an inhibitor of soluble guanylate cyclase) on the vasorelaxant response to nociceptin on rat aortic rings (with intact endothelium) in vitro precontracted with U44619, a thromboxane $A_2$ mimic.

Figure 12:
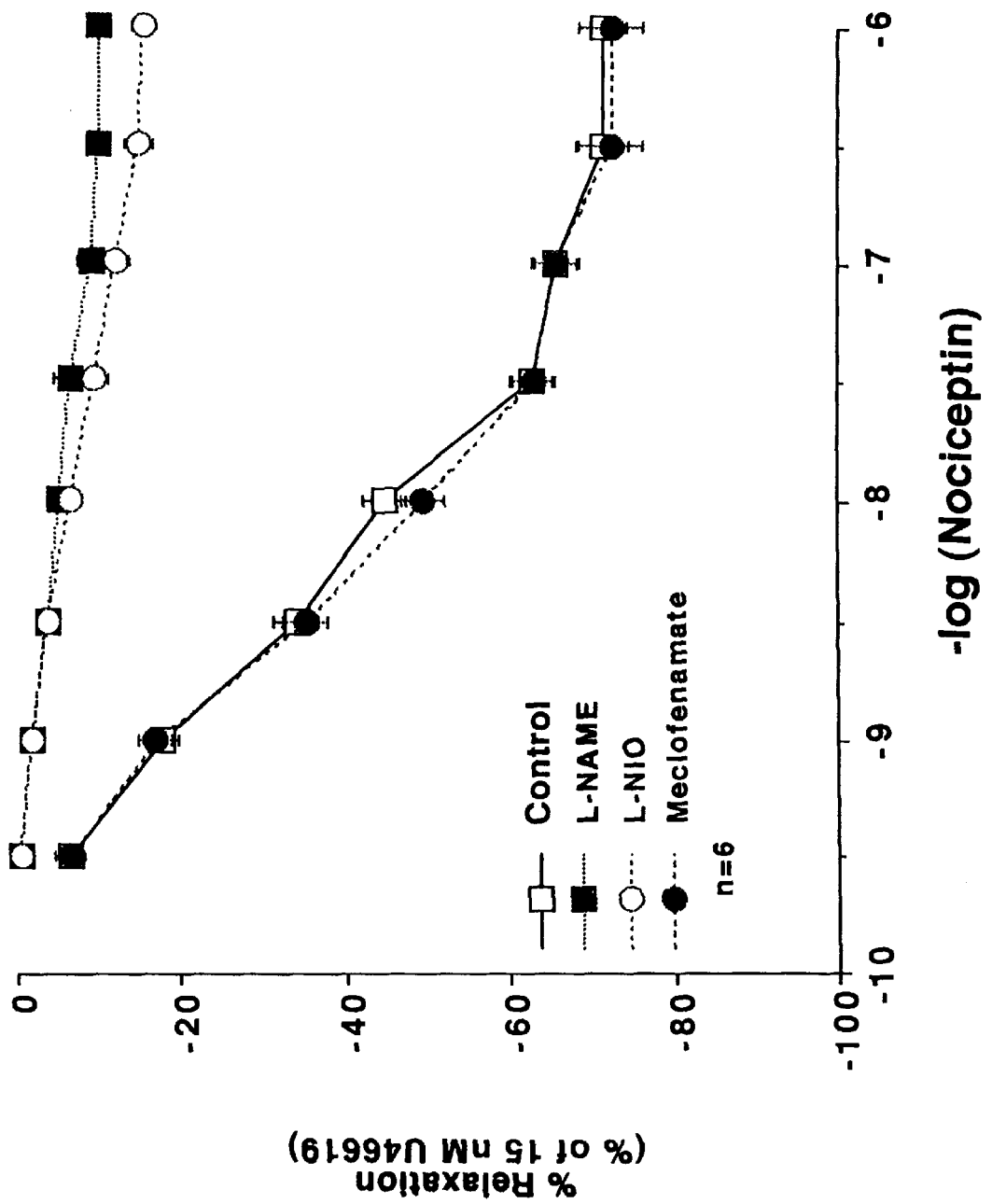

FIG. 12 illustrates the influence of L-nitro-arginine methyl esther (L-NAME), L-$N^5$-(1-iminoethyl) ornithine (L-NIO), and sodium meclofenamate on the aortic vasorelaxant response to nociceptin. Rat aortic rings in vitro (with intact endothelium) were precontracted with U44619, a thromboxane $A_2$ mimic.

Figure 13:
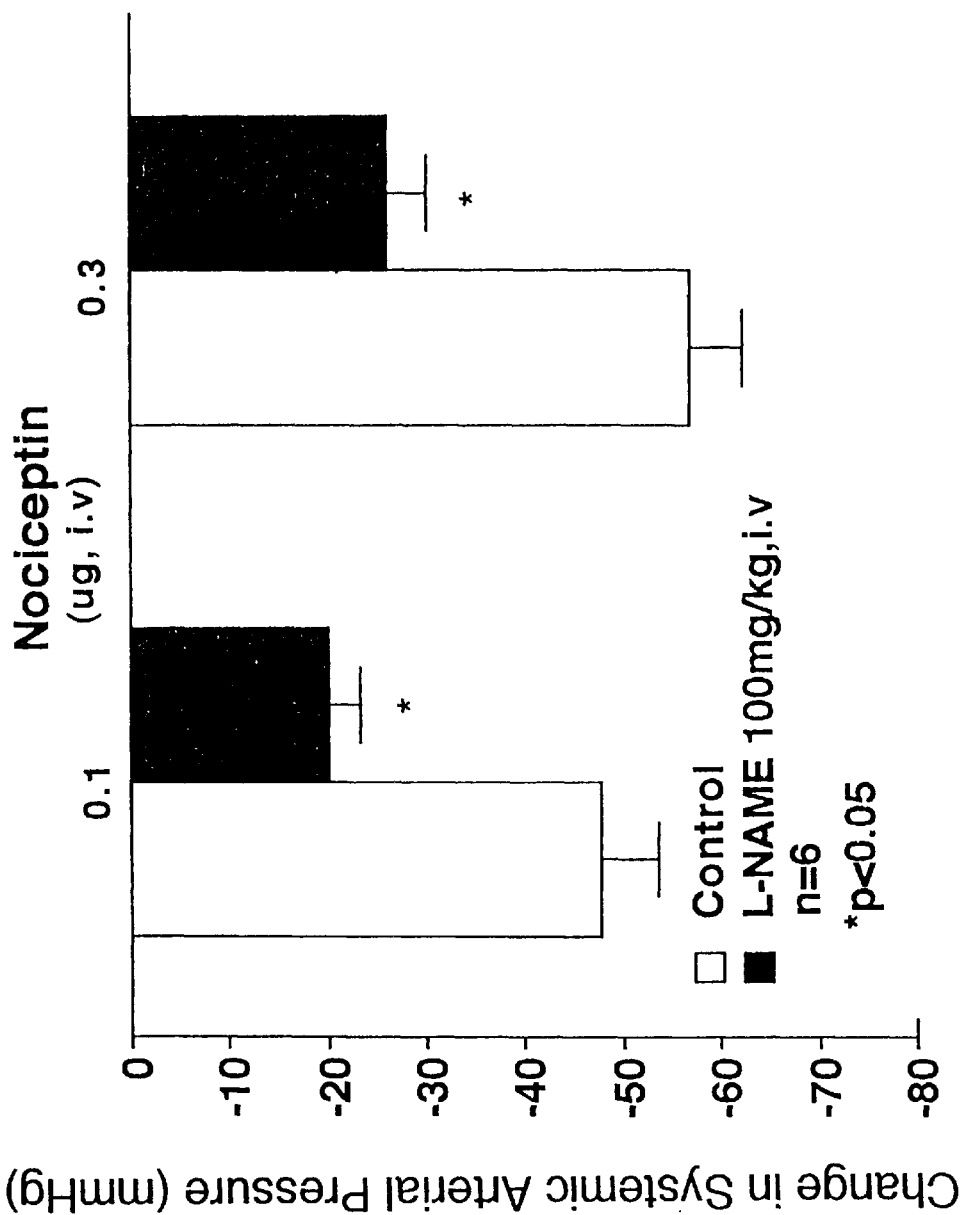

FIG. 13 illustrates the effects of bolus intravenous (i.v.) administration of nociceptin on systemic arterial pressure in the anesthetized rat in vivo before and after administration of L-nitro-arginine methyl ester (L-NAME), an inhibitor of constitutive nitric oxide synthase. N=number of animals. *$p<0.05$ when compared to corresponding control value.

Figure 14:
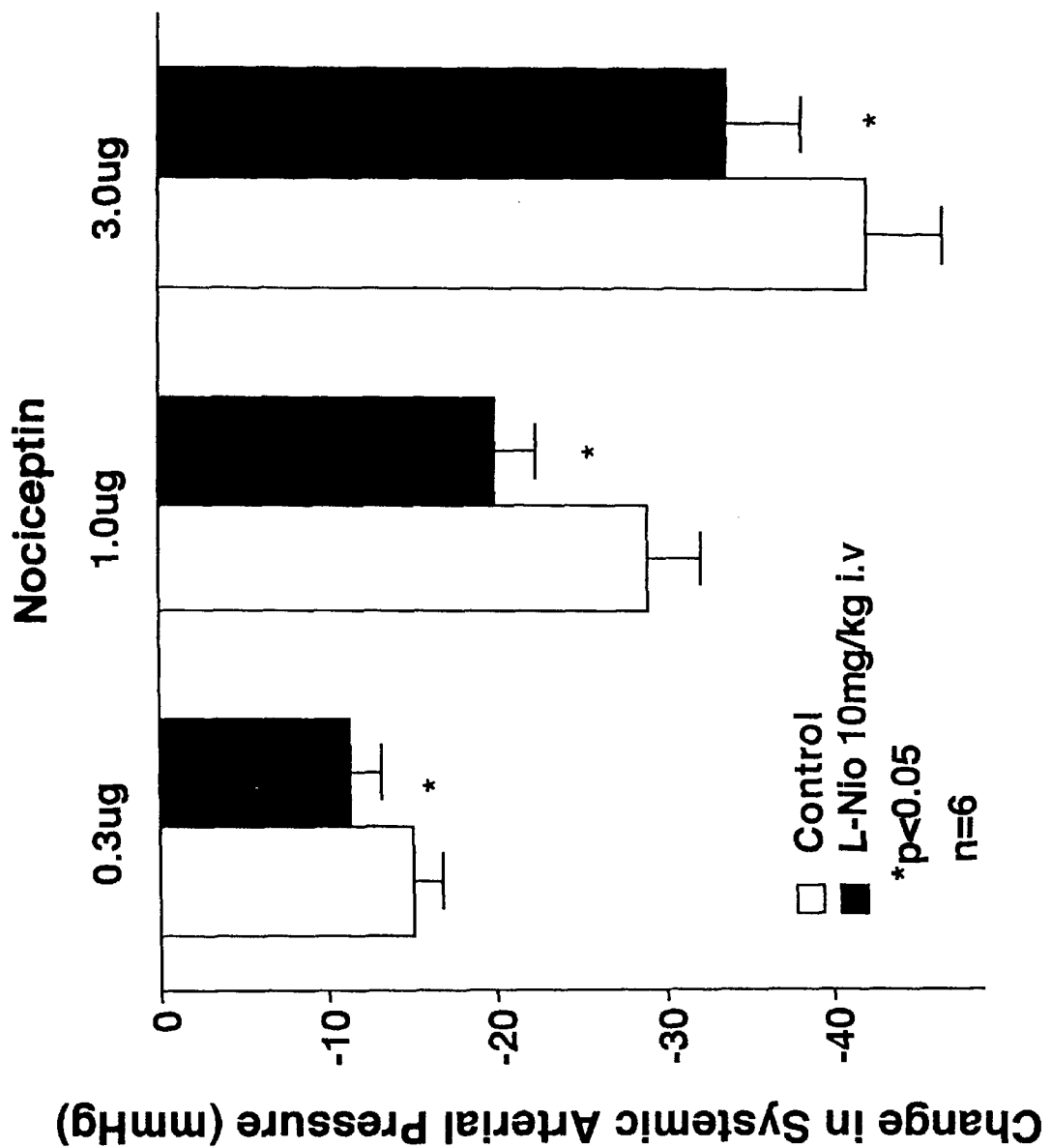

FIG. 14 illustrates the effects of bolus intravenous (i.v.) administration of nociceptin on systemic arterial pressure in the anesthetized rat in vivo before and after administration of L-$N^5$-(1-iminoethyl) ornithine (L-NIO), an inhibitor of constitutive nitric oxide synthase. N=number of animals. *$p<0.05$ when compared to corresponding control value.

Figure 15:
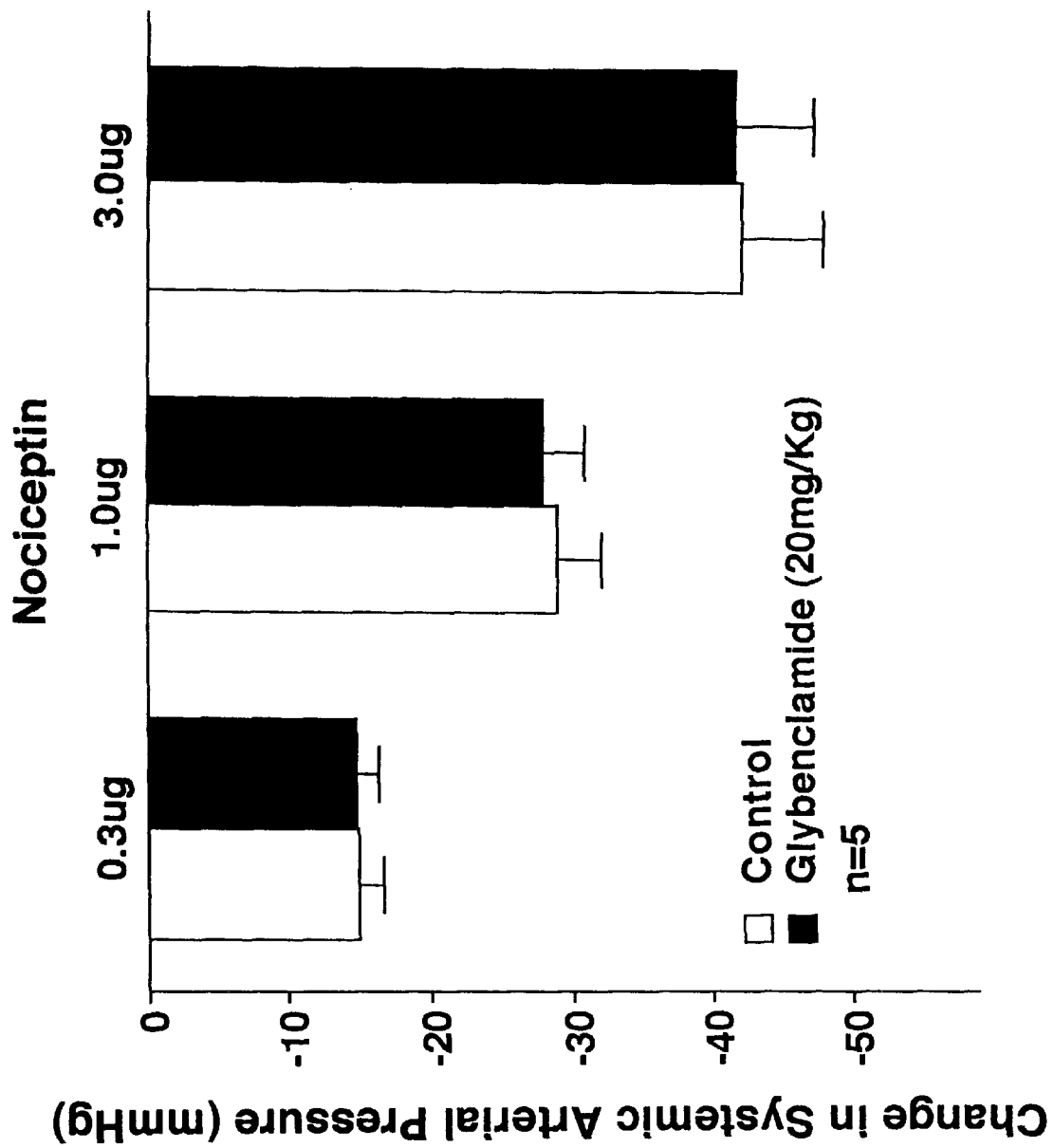

FIG. 15 illustrates the influence of intravenous (i.v.) administration of A) glybenclamide (an inhibitor of ATP-dependent potassium channels), and B) sodium meclofenamate (a cycloxygenase inhibitor including inhibition of prostacyclin formation) on the systemic vasodepressor response in vivo to bolus intravenous (i.v.) administration of nociceptin into rats anesthetized with sodium pentobarbital. N=number of animals.

Figure 16:
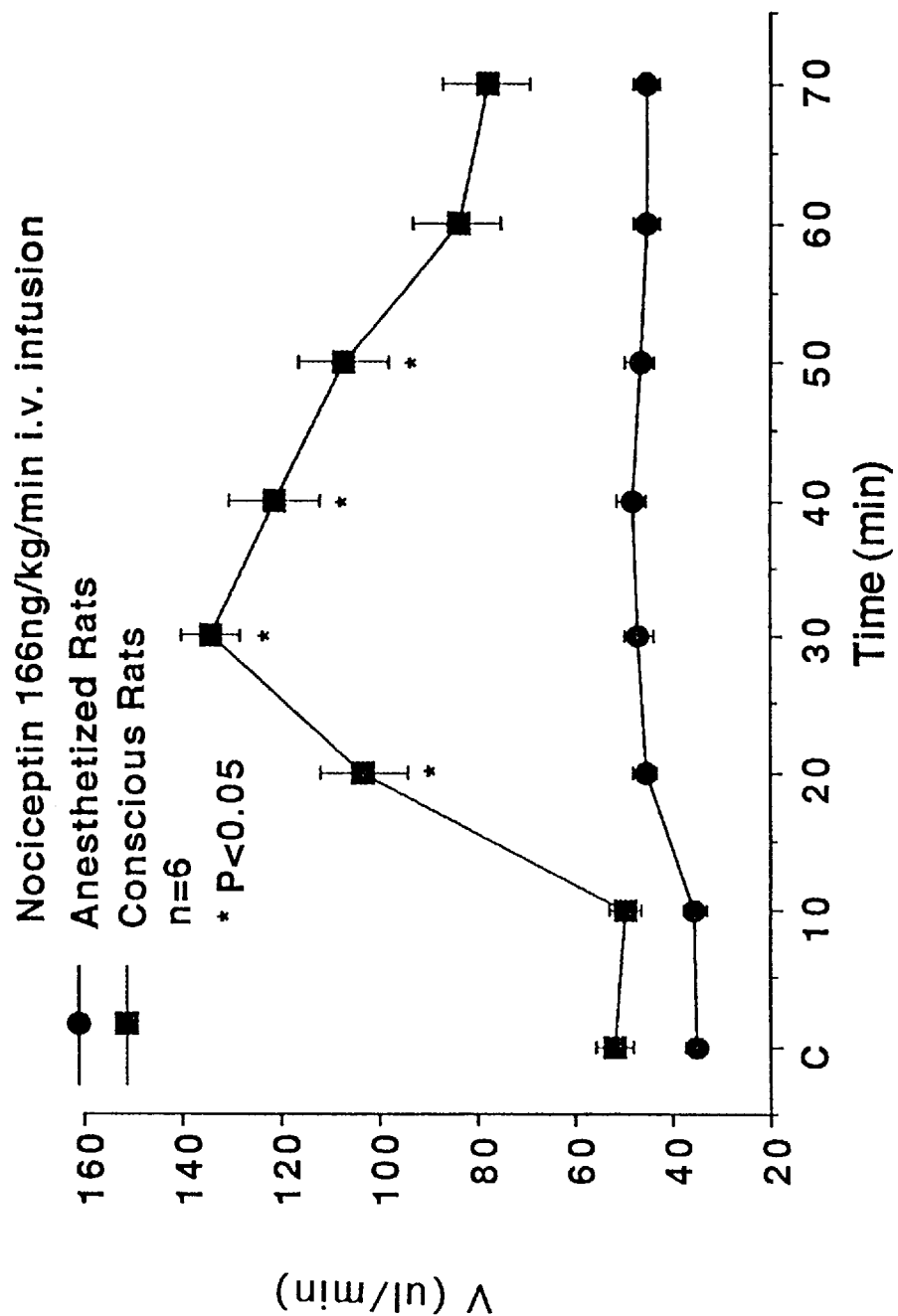

FIG. 16 compares the effects of intravenous (i.v.) infusion of nociceptin on urine flow rate (V) in conscious rats and rats anesthetized with sodium pentobarbital. N=number of rats. *$\leq 0.05$ significant when compared using ANOVA.

Figure 17:
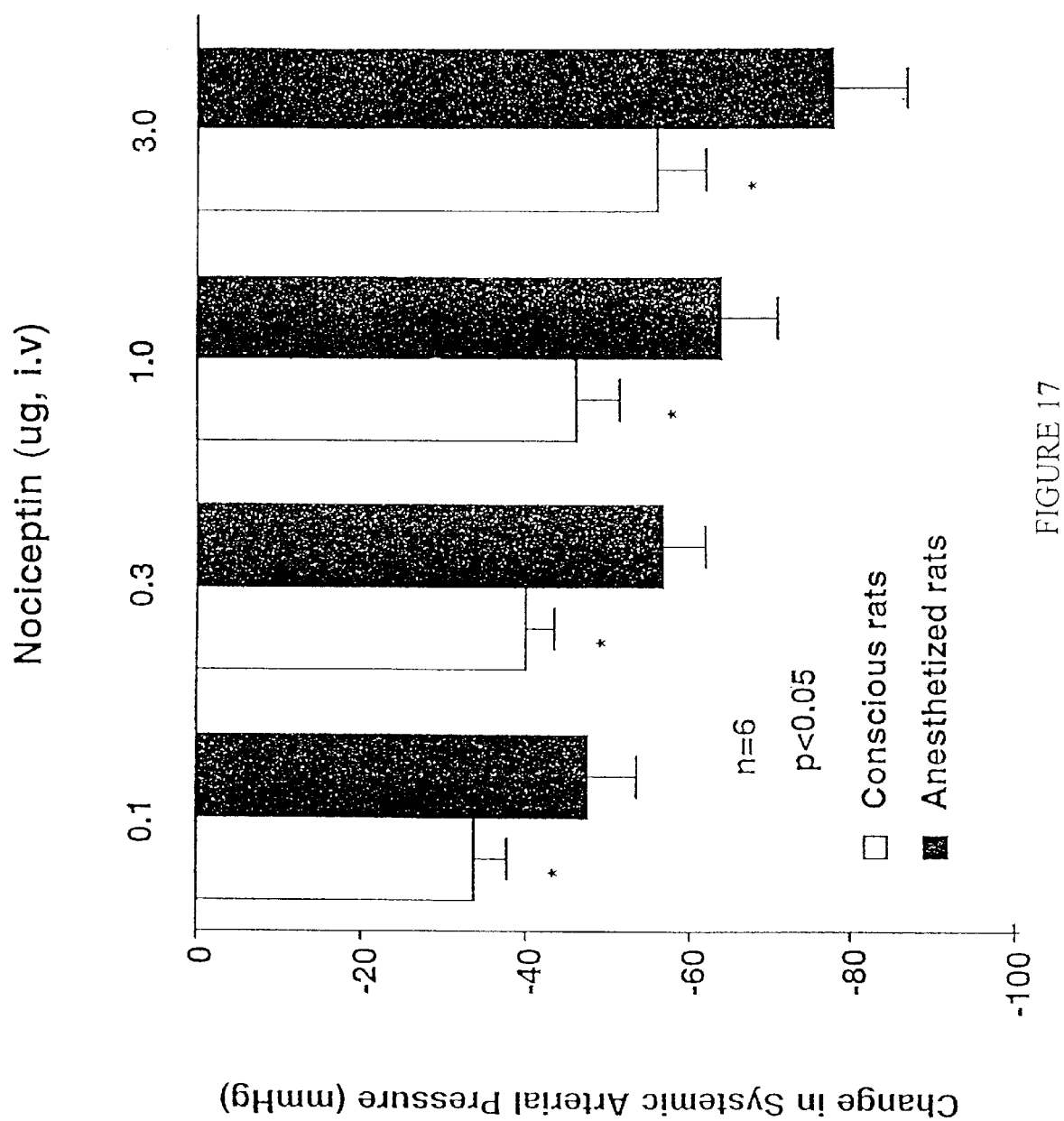

FIG. 17 compares the decrease in systemic arterial pressure in response to bolus intravenous (i.v.) injections of nociceptin into conscious rats and rats anesthetized with sodium pentobarbital. N=number of animals. *≦0.05 when ANOVA used statistical comparison.

Figure 18:
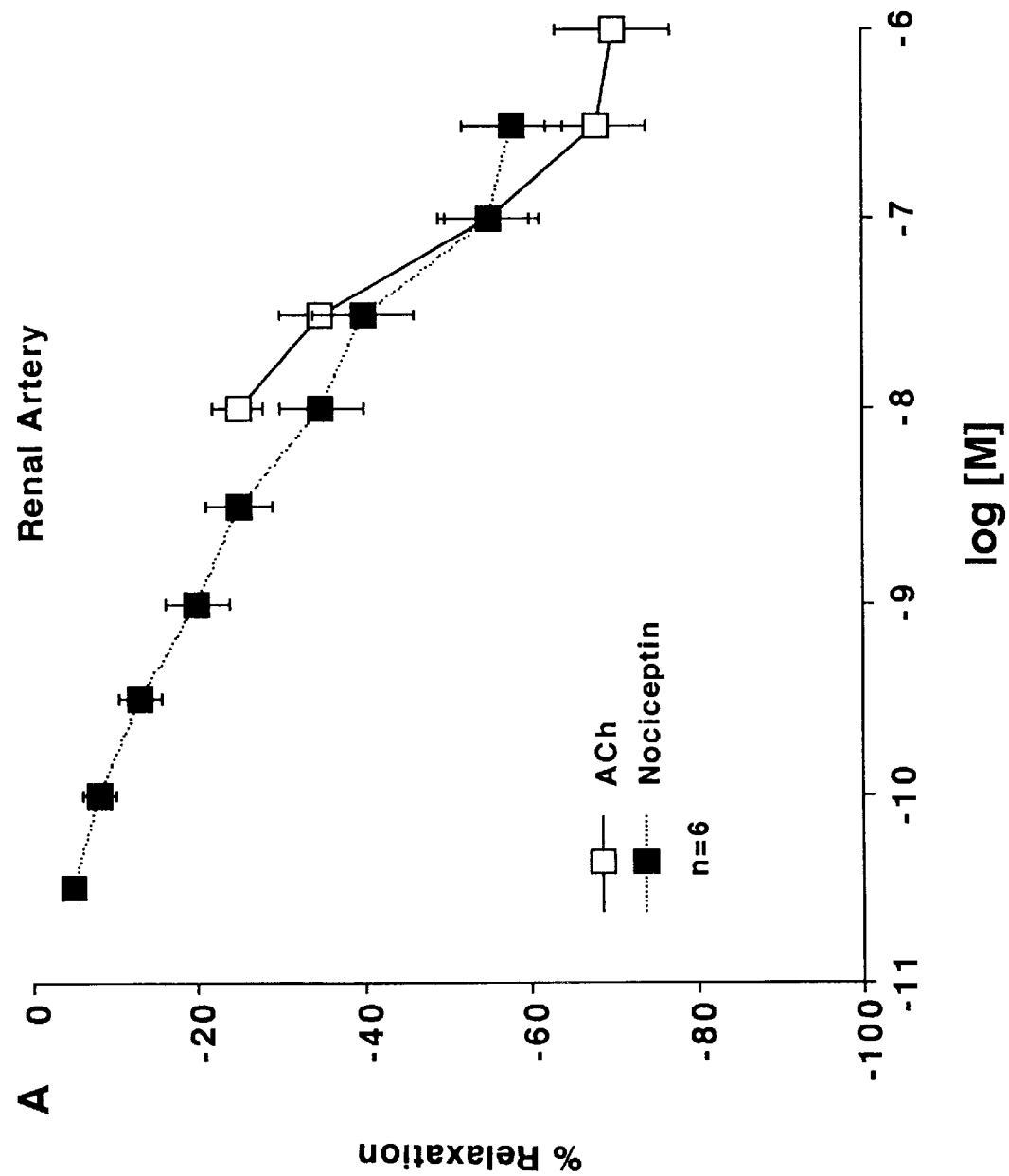

FIG. 18 illustrates the effects of acetylcholine (Ach) and nociceptin on isolated feline renal arterial rings (with endothelium) in vitro precontracted with phenylephrine, an alpha$_1$ adrenoceptor agonist. N=number of animals.

Figure 19:
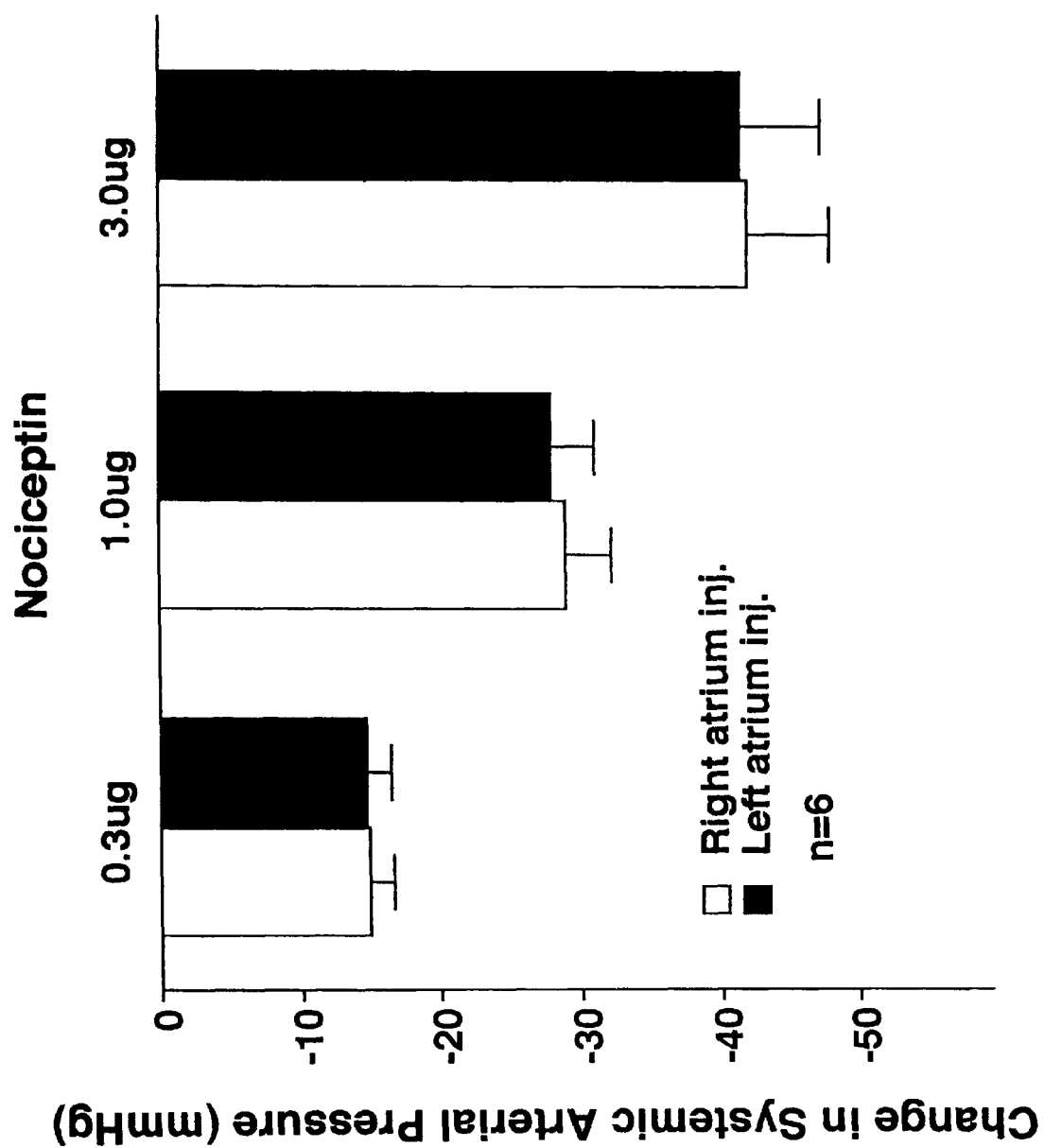

FIG. 19 compares the effects of bolus administration of nociceptin into the right atrium and left atrium on systemic arterial pressure in the anesthetized rat in vivo. N=number of animals.

Figure 20:
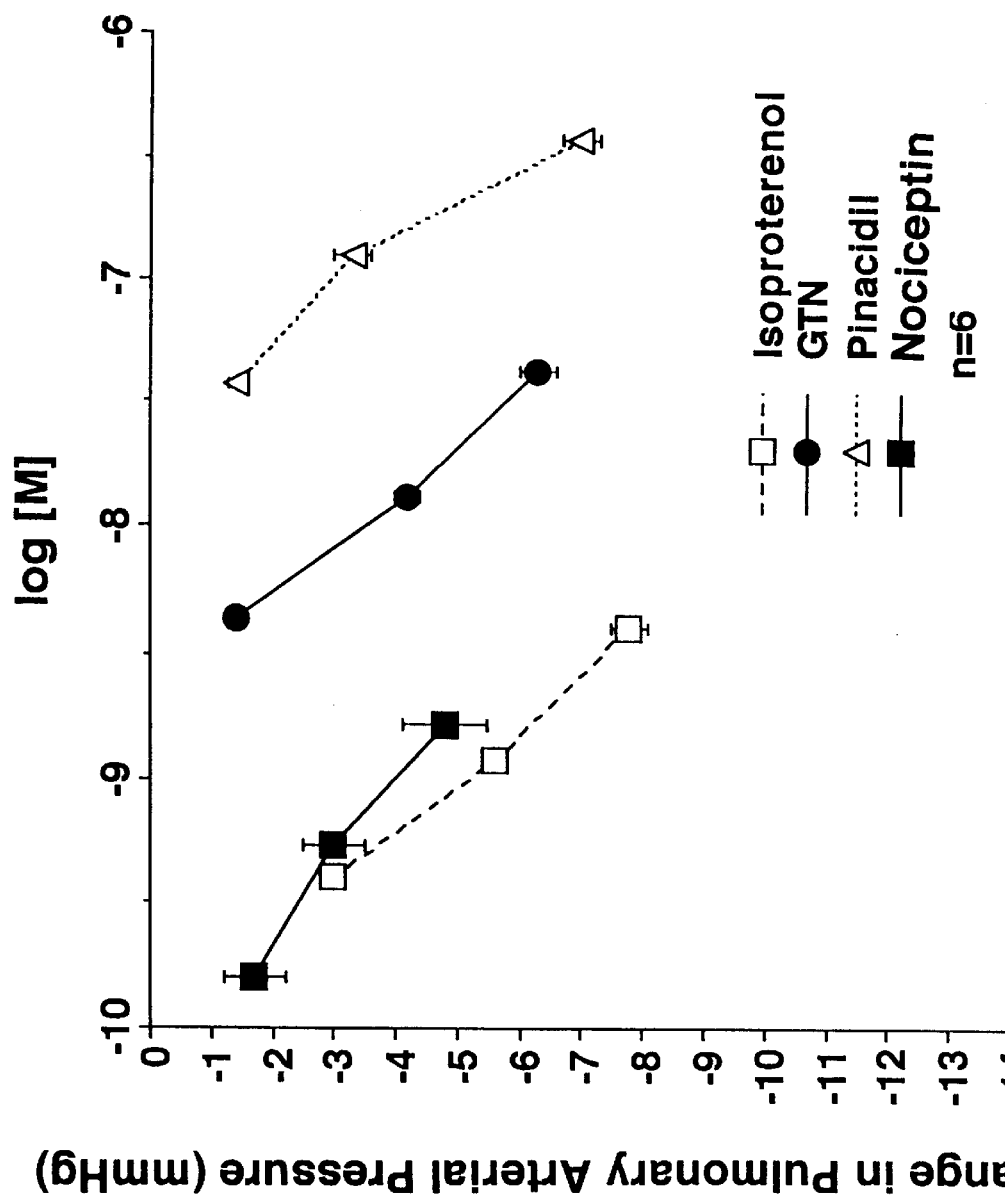

FIG. 20 illustrates the relative pulmonary vasodepressor activity in response to intralobar arterial bolus injections of isoproterenol (a beta$_2$ adrenoceptor agonist), nitroglycerin (GTN), pinacidil (an agonist for ATP-dependent potassium channels), and nociceptin in the pulmonary vascular bed of the intact-chest, anesthetized rat under conditions of elevated pulmonary vasomotor tone. Since pulmonary blood flow and left atrial pressure were held constant, the decreases in pulmonary artery pressure directly reflect decreases in pulmonary vascular resistance. N=number of animals.

Figure 21A:
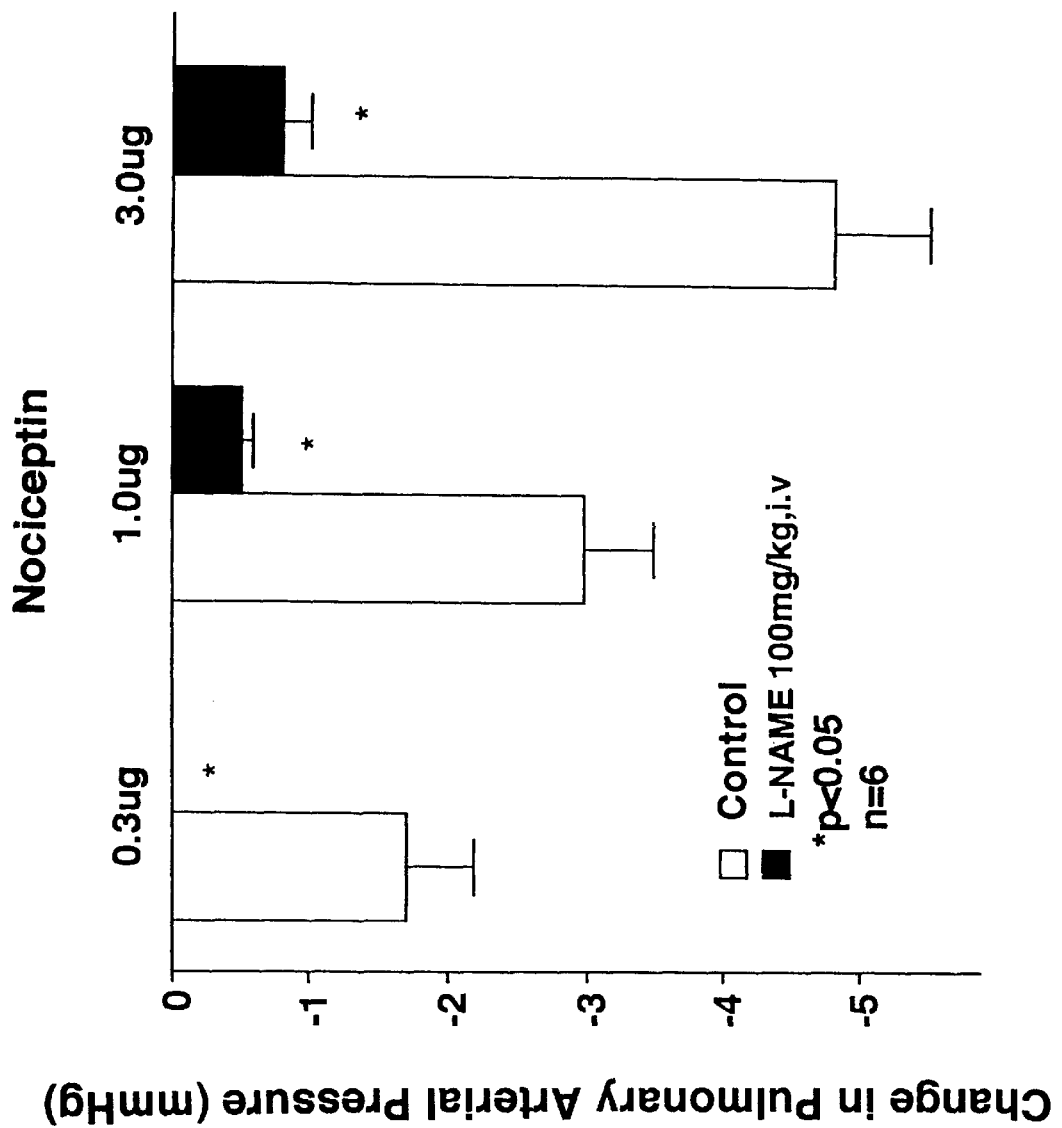
Figure 21B:
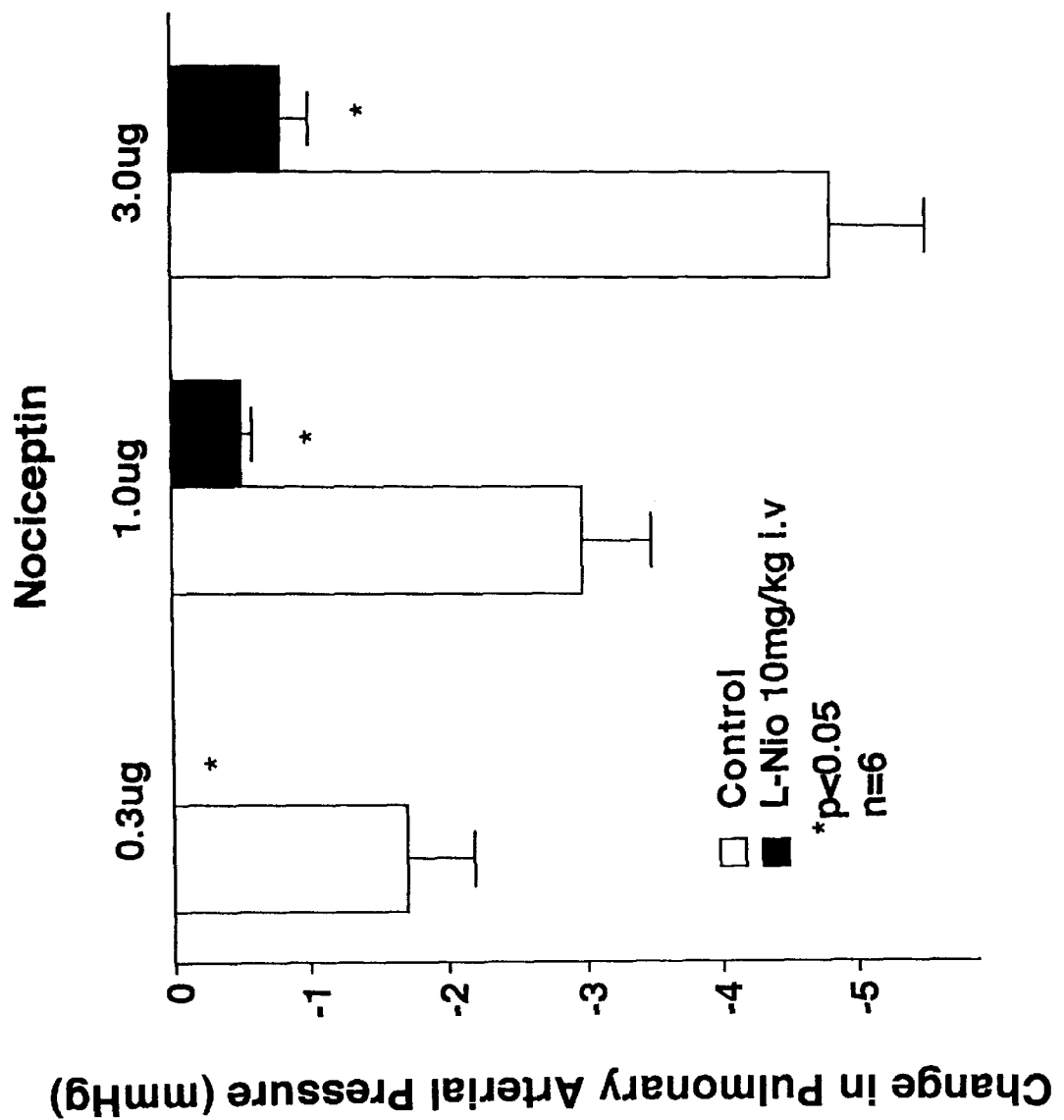

FIG. 21 illustrates the influence of A) L-nitro-arginine methyl ester (L-NAME) and, B) L-N$^5$-(1-iminoethyl) ornithine (L-NIO) on the pulmonary vasodilator response to intralobar arterial bolus injections of nociceptin into the pulmonary vascular bed of the intact-chest, anesthetized rat under conditions of elevated pulmonary vasomotor tone.

DETAILED DESCRIPTION OF INVENTION

Specifically, clinical use of wild-type nociceptin (SEQ ID NO. 1) administered orally, intravenously, via the skin, or intranasally, provides an important therapeutic alternative in the management of edematous states of the lung, including congestive heart failure, drowning and adult respiratory distress syndrome (ARDS).

In an embodiment of the present invention, wild-type nociceptin is effectively administered to humans transdermally via patches in combination with one or more pharmaceutically acceptable carriers.

In the method of the instant invention, wildtype nociceptin is physiologically active in vivo and produces marked changes in the renal excretion of water and sodium. For example, in conscious Sprague-Dawley rats, intravenous infusion of nociceptin produced a profound increase in urine flow rate and a decrease in urinary sodium excretion. Additionally, intracerebroventricular (i.c.v.) microinjection of nociceptin into conscious rats produced a concurrent diuresis (dose-dependent) and antinatriuresis. The magnitude and pattern of the central nociceptin-induced water diuresis was similar to that produced by i.c.v. dynorphin A. Whereas i.c.v. pretreatment with the selective kappa-opioid receptor antagonist nor-binaltorphimine completely prevented the renal responses produced by dynorphin A, this antagonist did not alter the diuresis or antinatriuresis produced by central nociceptin.

Thus, the results of the practice of the method of the instant invention show that in conscious rats, nociceptin produces a selective water diuresis via a central nervous system mechanism independent of kappa-opioid receptors. Together, the practice of the method of the present invention suggests that endogenous wild-type nociceptin is a novel peptide involved in the central control of water balance and ultimately in the regulation of arterial blood pressure.

Endogenous opioid peptides have been categorized into three families, 1) endorphins (e.g. β-endorphin, α-neoendorphin), 2) enkephalins (e.g. leucine enkephalin, methionine enkephalin) and 3) dynorphins (e.g. dynorphin A) (1). Although the selectivity of these natural opioids is only modest, these peptides are suggested to be the endogenous ligands for the mu, delta, and kappa-opioid receptors, respectively (1). In addition to these classical subtypes, cDNA expression cloning techniques have been used to isolate and identify a fourth opioid receptor subtype in human, rat and mouse brain cDNA libraries. This orphan receptor, referred to herein as ORL$_1$ (opioid receptor-like one) (2), but also termed LC132, XOR-1, ROR-C, XOR, Hyp 8-1, C3, or oOR (3), is suggested to represent a novel member of the opioid receptor family. This premise is supported by the observation that ORL$_1$ shares a high degree of nucleotide sequence homology in the transmembrane domains with the cloned mu, delta, and in particular, kappa-opioid receptor subtypes (2,3).

In the fall of 1995, the endogenous ligand for ORL$_1$ was isolated from brain tissue by two independent groups of investigators. This novel peptide has been referred to by Meunier et al. (4) as nociceptin, but also termed Orphanin FQ by Reinscheid et al. (5). Nociceptin binds to ORL$_1$ in a saturable manner and with high affinity, thus providing support for this peptide as the endogenous ligand of ORL$_1$ (5). On the surface, nociceptin bears the closest resemblance to members of the opioid peptide family. Nociceptin is a heptadecapeptide with an amino acid sequence similar to that of endogenous opioid peptides, most notably dynorphin A (4,5). Characteristic of dynorphin A and other opioid ligands, nociceptin inhibits forskolin-stimulated cAMP production (4,5).

Despite these similarities, however, it appears that nociceptin may have actions different than those typically produced by endogenous opioids. For instance, Meunier et al. (4) and Reinscheid et al. (5), reported that administration of nociceptin to mice produced a hypersensitivity to painful stimuli, rather than producing an analgesic response characteristic of opioids.

In vivo studies in conscious animals and man indicate that opioid agonists produce profound changes in cardiovascular (1,6) and renal excretory function (7). In this regard it is well established that peripheral or central administration of kappa-opioid agonists produce a marked free-water diuresis (7,8).

Because of the similarities between nociceptin and ORL$_1$ to those of the endogenous opioid systems (in particular dynorphin A and the kappa-opioid receptors), the inventive hypothesis that nociceptin is active in vivo and produces changes in cardiovascular and renal functions was tested. For this purpose, the cardiovascular and renal responses produced by intravenous (i.v.) infusion of nociceptin were examined in conscious chronically instrumented Sprague-Dawley rats (see Example 1). The results (FIG. 2) demonstrate that i.v. infusion of nociceptin produced a profound increase in urine flow rate and decrease in urinary sodium excretion. These renal responses were slow in onset, of approximately 70 min duration, with peak changes occurring approximately 40 min after the start of nociceptin infusion. In previous studies under similar experimental conditions (see Example 2), i.v. infusion of the selective kappa-opioid receptor agonist, U-50,488H (20 μg/kg/min), produced a similar pattern of changes in the renal excretion of water and sodium (i.e. diuresis and antinatriuresis). In the present studies, i.v. infusion of nociceptin also produced a slight, but statistically significant decrease in mean arterial pressure that was sustained throughout drug infusion. Despite the decrease in mean arterial pressure, nociceptin did not alter heart rate at any time period. In these studies, nociceptin did not produce any behavioral or sedative effects characteristic of higher doses of opioids.

$ORL_1$ transcripts have been shown to be expressed in brain regions known to participate in the regulation of blood pressure and fluid and electrolyte balance (e.g. the hypothalamus, amygdala, etc.) (3). To investigate whether nociceptin may affect cardiovascular and renal function from a central site of action, we examined the cardiovascular and renal responses produced by intracerebroventricular (i.c.v.) injection of nociceptin in conscious rats (see Example 2).

Preliminary studies demonstrated that 1 $\mu$g nociceptin was the minimum effective i.c.v. dose to evoke a change in urine flow rate and urinary sodium excretion in rats. As compared to respective group control levels (FIG. 3), i.c.v. injection of nociceptin at doses of 1, 10, or 30 $\mu$g produced significant ($p<0.05$) decreases in heart rate, mean arterial pressure and urinary sodium excretion. The bradycardia and hypotensive response produced by all doses were fast in onset (1–3 min) and persisted for approximately 30 to 40 minutes, respectively.

Central administration of nociceptin also produced a profound diuretic response in each group of animals, with the higher i.c.v. doses (10 and 30 $\mu$g) tending to have a slower time of onset. A group analysis of variance (ANOVA) confirmed that the peak diuresis produced by i.c.v. injection of 10 $\mu$g nociceptin (40 min) was significantly greater ($p<0.05$) than that produced by the 1 $\mu$g i.c.v. dose (30 min). Similarly, the cumulative urine output (total urine collected for 60 min starting 10 min after i.c.v. injection) produced by i.c.v. injection of 10 $\mu$g nociceptin (7,740±920 $\mu$l) was significantly (ANOVA, $p<0.05$) greater than that produced by the 1 $\mu$g dose (4,660±250 $\mu$l) (30 $\mu$g cumulative urine output, 6060±670 $\mu$l).

Subsequent studies on renal functional and urine flow rate showed that the effects of nociceptin are apparent at doses approximately 120-fold lower than the preliminary studies described above. The subsequent and more complete studies were confirmed using three different commercially available sources of nociceptin (see Example 5) and provide evidence that nociceptin has an even greater and more potent diuretic activity than originally suspected.

In additional studies, it was observed that tachyphylaxis to the cardiovascular (bradycardia and hypotension) and renal responses (diuresis and antinatriuresis) produced by i.c.v. nociceptin (1, 10 or 30 $\mu$g) did not develop following a consecutive i.c.v. injection of the same dose of nociceptin. In contrast to these responses, in other animals i.v. bolus administration of 30 $\mu$g nociceptin did not alter any cardiovascular or renal parameter, thereby excluding the possibility that centrally administered nociceptin affected cardiovascular or renal function subsequent to its leakage into the periphery.

Figure 4:
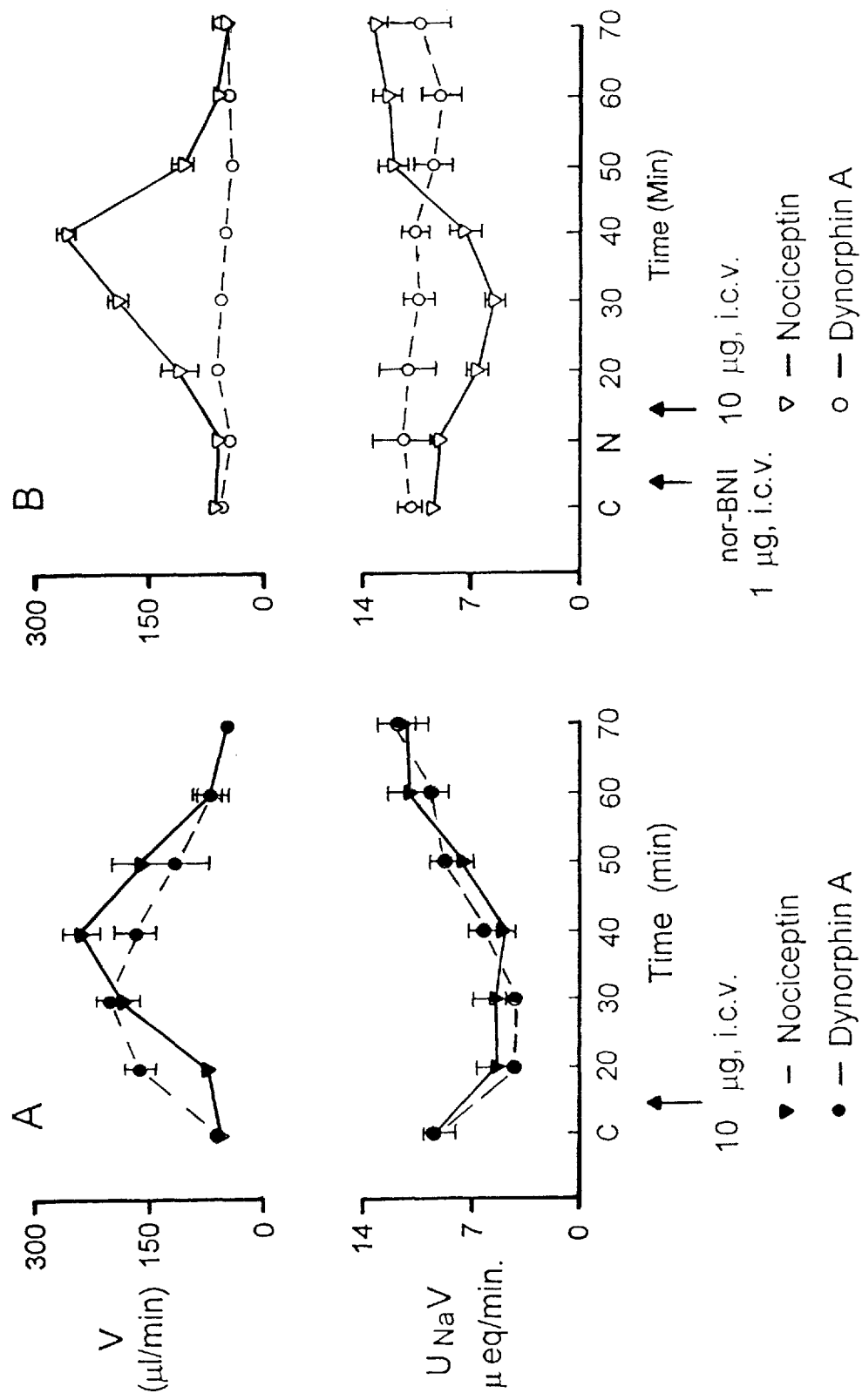
FIG. 4 shows the renal excretory effects of bolus intracerebroventricular (i.c.v.) administration of nociceptin or dynorphin A in conscious (A) naive rats, and (B) in separate groups of rats pre-treated intracerebroventricular (i.c.v.) with the selective kappa-opiold receptor antagonist, nor-binaltorphimine.

The renal responses (i.e. diuresis and antinatriuresis) evoked by i.v. (FIG. 2) or i.c.v. (FIG. 3) nociceptin in conscious rats, closely resembles the pattern of changes in renal excretory function produced by peripheral or central administration of a selective kappa-opioid receptor agonist (e.g. U-50,488H, U-69,593, CI-977, bremazocine, tifluadom) (7,8,10). This observation is of interest since the amino acid sequence of nociceptin is suggested to be most similar to that of the endogenous opioid peptide dynorphin A, the proposed endogenous ligand of kappa-opioid receptors, FIG. 1 (4,5,11). To determine whether nociceptin affects the renal handling of water and sodium via activation of central kappa-opioid receptors, the renal responses produced by central nociceptin were studied in conscious rats pre-treated i.c.v. with the selective kappa-opioid receptor antagonist, nor-binaltorphimine (9,12). For comparative purposes, the renal responses produced by central administration of the endogenous opioid peptide, dynorphin A, were also studied i.c.v. Administration of 10 $\mu$g nociceptin (data from FIG. 3 superimposed in FIG. 4A) or 10 $\mu$g dynorphin A (FIG. 4A) produced a concurrent diuretic and antinatriuretic response in conscious rats. Whereas these two peptides evoked similar peak increases in urine flow rate and decreases in urinary sodium excretion, the onset of diuresis produced by nociceptin was significantly delayed ($p<0.05$ at time 20 min) (FIG. 4A). In separate animals (FIG. 4B), i.c.v. pretreatment with the selective kappa-opioid receptor antagonist nor-binaltorphimine completely prevented the diuresis and antinatriuresis produced by dynorphin A.

While the inventors do not wish to be tied to a particular theory for the method of the present invention, these findings are consistent with the notion that kappa-opioid agonists invariably produce a diuretic (and antinatriuretic) response by a pathway that involves activation of kappa-opioid receptors (7,12). In contrast, i.c.v. pretreatment with nor-binaltorphimine did not alter the diuretic or antinatriuretic profile of central nociceptin (FIG. 4B). Together, these results clearly demonstrate that nociceptin affects handling of water and sodium by a central pathway independent of kappa-opioid receptors.

In the present invention, it has been demonstrated that wild-type nociceptin is functionally active in vivo, and is capable of producing profound changes in the renal excretion of water and sodium following administration into the periphery or central nervous system. Further, although nociceptin has a number of similarities with dynorphin A (4,5, 11), the results of the present invention indicate that nociceptin is unique from the endogenous opioid ligand dynorphin A, at least in that nociceptin is capable of producing a centrally mediated free-water diuresis via a pathway independent of kappa-opioid receptors. This finding is of importance, inter alia, physiologically, since to date, opioids are the only known endogenous substance which produce a selective water diuresis.

In addition to a physiological interest, the results of the present invention are also of great importance from a therapeutic standpoint. Currently, there are no solute-free water diuretics (i.e. aquaretics) available for clinical use for the management of hyponatremic states such as the syndrome of inappropriate secretion of antidiuretic hormone (SIADH) or other potentially life-threatening water-retaining diseases including congestive heart failure, cirrhosis with ascites, or adult respiratory distress syndrome (ARDS). While kappa-opioid receptor agonists (e.g. enadoline, spiradoline) have the potential to be clinically effective for this use, these agents produce a central nervous system side effect referred to as dysphoria (a sensation of dizziness, emotional lability and abnormal thinking) in patients (12). Since the dysphoria is mediated by activation of central kappa-oploid receptors (13), in the method of the present invention, nociceptin is devoid of producing dysphoria, yet retains its therapeutic water diuretic properties. In this regard, the present invention offers the first clinically useful therapeutic tool for the management of hyponatremic and water-retaining diseases.

The following Examples are presently solely for illustrative purposes and in no manner are indented to limit the scope of the invention.

EXAMPLE 1
PREPARATION OF WILDTYPE NOCICEPTIN

OFQ peptide was synthesized on a CS Bio automated peptide synthesizer using the Merrifield solid phase strategy and Boc chemistry. All amino acids were N-terminal Boc derivatives and coupled to the resin (1 mM/0.25 g, 0.4 mcq/g p-me-BHA) with equivalent amounts of BOP and DIEA. Boc-amino acids used for the synthesis and side chain protecting groups are: Gln(Xan), Asn(San), Lys(Cl-Z), Arg (Tos), Ser(OBzl) and Thr(OBzl). Completeness of coupling was determined by the ninhydrin test. Automated program for the synthesis of OFQ carried out the following steps: 1. The resin was washed two times 1 minute each with ~100 ml methylene chloride ($CH_2Cl_2$). All solvent volumes in this synthesis were adjusted such that they were at least twice the volume of the wet resin, 2. Pretreatment of the resin once for 1 minute with 40% trifluoroacetic acid (TFA)/$CH_2Cl_2$ with 1% indole, 3. Deprotection, removal of the N-terminal tert-butyloxycarbonyl (Box) protecting group, was achieved by mixing the resin for 25 minutes with 40% TFA/$CH_2Cl_2$ with 1% indole, 4. Resin washed once for 1 minute with $CH_2Cl_2$, 5. Resin washed once for 1 minute with methanol (MeOH), 6. Resin washed twice 1 minute each with $CH_2Cl_2$, 7. The resin was prewashed once for 1 minute with 10% disopropylethylamine (DIEA) in $CH_2Cl_2$, 8. Neutralization of the protonated N-terminal of the growing peptide chain achieved by mixing the resin for 5 minutes with 10% DIEA/$CH_2Cl_2$, 9. Coupling of the next appropriate amino acid was achieved by the addition of 3 equivalents (3 mM) of Boc-amino acid, benzotriazol-1-yl-oxy-tris (dimethylamino) phosphoniumhexafluorophosphate (BOP) and DIEA in a 3:1 mixture of dimethylformamide (DMF) and $CH_2Cl_2$ (excepting Boc-Gln and Asn, which were dissolved in 9:1 DMF and $CH_2Cl_2$). The coupling reaction time was 80 minutes. The above cycles were repeated for the addition of each amino acid in the sequence of OFQ.

The peptide was cleaved from the resin using HF (hydrogen fluoride) methodology. Two point two grams of OFQ peptidyl resin was added to an HF reaction vessel with 2.2 ml anisole and 0.2 ml dimethyl sulfide (DMS) (1 ml anisole/gram peptidyl resin and 0.1 ml DMS/gram peptidyl resin) and the reaction vessel attached to a Type II HF reaction apparatus. The reaction vessel containing the resin mixture was cooled to −50° C. in a dry ice/acetone bath and 10 ml of HF (5 ml HF/gram peptidyl resin) added to the mixture. The temperature was allowed to rise to, and maintained at 0° C., with a water ice bath. The HF/resin mixture was stirred at 0° C. for 45 minutes, then evacuated to dryness. The resin was washed four times each with ~30 ml diethyl ether ($Et_2O$). OFQ peptide was extracted from the resin with 60 ml distilled $H_2O$ and 30 ml acetonitrile and lyophilized.

HF crude OFQ was purified with preparatory HPLC (Shimadzu SCL-10A system controller, SPD-10A uv-vis detector and two LC-8A preparative pumps with manual injection). 2 g lyophilized HF crude OFQ was loaded onto a preparative C-18 HPLC (C-18 column=10μ, 1 inch diameter, 17 inches length; uv wavelength=220 nm) and eluted with Buffer A (0.1% TFA; 999 ml deionized $H_2O$ and 1 ml TFA) to Buffer B (60% $CH_3CN$/0.1% TFA; 600 ml $CH_3CN$, 399 ml deionized $H_2O$ and 1 ml TFA) over 120 minutes at a flow rate of 9 ml/minute. Fractions were collected at two minutes per tube (total 18 ml/tube). Pure OFQ (0.98% as determined by analytical HPLC, linear gradient of 100% Buffer A to 100% Buffer B over 40 minutes at a flow rate of 1 ml/minute; uv detector wavelength 220 nm; Vydac C-18 columns-5μ, 4.6 mm×25 mm. Analytic HPLC system is Shimadzu SCL-10A system controller, SPD-10A uv-vis detector. SIL-10A auto injector and two LC-10AS high pressure pumps.) was lyophilized and exhibited correct mass spectrum, MW=1809.

EXAMPLE 2
METHODS FOR ADMINISTRATION OF NOCICEPTIN TO ANIMALS

Anesthetized male Sprague-Dawley rats (275–300 g, Sprague-Dawley, Inc., Indianapolis, Ind.) were implanted with chronic arterial and venous cannulas and a bladder catheter in accordance with previously published methods (10, 12). For experiments in which drugs were administered i.c.v., a stainless steel cannula was stereotaxically implanted into the right lateral ventricle of rats under anesthesia at least 5–7 days prior to experimentation (11). On the morning of the study rats were placed in a rat holder which permits forward and backward movement and allows for collection of urine from the bladder catheter. Conscious rats were then infused i.v. with isotonic saline (50 μl/min) for the duration of the experiment. The arterial cannulae was then flushed and attached to a pressure transducer (Statham P23Db) and the urinary bladder catheter led to a collection beaker. After equilibration and stabilization of urine flow rate and urinary sodium excretion (approximately 2–3 hours) the experimental protocol described in each figure legend commenced. Intravenous and i.c.v. stock solutions of nociceptin and nor-binaltorphimine were prepared fresh in isotonic saline vehicle. The i.v. infusion dose of nociceptin (20 μ/kg/min) was derived from previous studies (see Example 2) in which we examined the renal responses produced by i.v. infusion of the selective kappa-opioid agonist, U-50,488H. Microinjection of nociceptin (1, 10 or 30 μg total in 3 μl isotonic saline) or nor-binaltorphimine (1 μg total in 3 μl isotonic saline) into the lateral cerebral ventricle of conscious rats was made via a 10 μl Hamilton syringe. The i.c.v. dose of nor-binaltorphimine was derived from previous investigations (11) in which we demonstrated that i.c.v. pretreatment of rats with 1 μg nor-binaltorphimine completely and selectively prevented the renal responses produced by i.c.v. microinjection of the selective kappa-opioid agonist, U50, 488H (1 μg). Animal experimentation and care procedures were in accordance with the National Institutes of Health guidelines for the care and use of animals.

EXAMPLE 3
TIME COURSE OF RESPONSES PRODUCED I.V. INFUSION OF NOCICEPTIN

Figure 2:
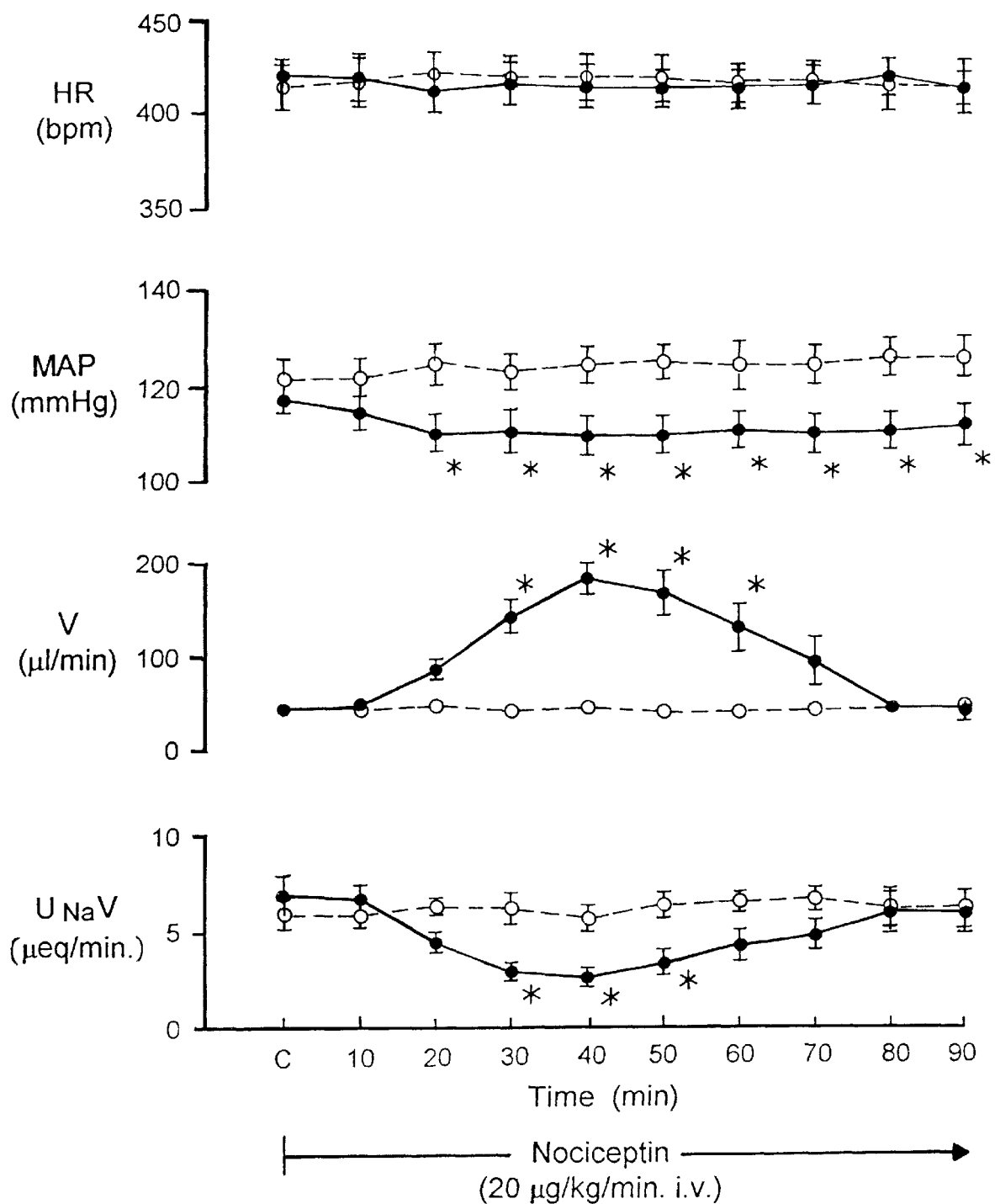
FIG. 2 shows the time course of cardiovascular and renal responses produced by intravenous (i.v.) infusion of nociceptin (20 µg/kg/min) into conscious rats.

FIG. 2 shows the time course of cardiovascular and renal responses produced by intravenous infusion of nociceptin or isotonic saline vehicle. As shown in FIG. 2, the cardiovascular and renal responses produced by intravenous (i.v.) infusion of nociceptin were examined in conscious chronically instrumented Sprague-Dawley rats (see Example 2). Values are means±S.E., illustrating the changes in heart rate (HR), mean arterial pressure (MAP), urine flow rate (V) and urinary sodium excretion ($U_{Na}V$) produced by continuous i.v. infusion of isotonic saline vehicle (○; 50 μl/min; n=6) or the opioid-like peptide, nociceptin (●; 20 μ/kg/min; n=6). Urine samples were collected during control (C, 20 min) and immediately after the start of nociceptin, or continued isotonic saline vehicle infusion for 90 min (consecutive 10-min urine samples). Statistical significance was determined by a repeated measure analysis of variance followed by a Bonferroni multiple comparisons test; asterisks denote a significant difference ($p<0.05$) from the respective group control.

EXAMPLE 4
SITE ACTION OF NOCICEPTIN

Preliminary studies demonstrated that 1 μg nociceptin was the minimum effective i.c.v. dose to evoke a change in urine flow rate (V) and urinary sodium excretion in rats. As compared to respective group control levels (FIG. 3), i.c.v. injection of nociceptin at doses of 1, 10, or 30 μg produced significant (p<0.05) decreased in heart rate, mean arterial pressure and urinary sodium excretion. The bradycardia and hypotensive responses produced by all doses were fast in onset (1–3 min) and persisted for approximately 30 to 40 minutes, respectively. Central administration of nociceptin also produced a profound diuretic response in each group of animals, with the higher i.c.v. doses (10 and 30 μg) tending to have a slower time of onset. A group analysis of variance confirmed that the peak diuresis produced by i.c.v. administration of 10 μg nociceptin (40 min) was significantly greater (p<0.05) than that produced by the 1 μg i.c.v. dose (30 min). Similarly, the cumulative urine output (total urine collected for 60 min starting 10 min after i.c.v. injection) produced by i.c.v. administration of 10 μg nociceptin (7.74±0.92 ml) was significantly (ANOVA, p<0.05) greater than that produced by the 1 μg dose (4.66±0.25 ml) [30 μg cumulative urine output, 6.06±0.67 ml].

Since direct right renal arterial administration of nociceptin did not increase left or right ureteral flow rate (See FIG. 5), the present data suggests nociceptin does not act directly on receptors in the kidney to increase urinary flow rate (V). This was further confirmed indirectly by additional studies demonstrating that the peak increases in and time courses of the urinary flow rates (V) in responses to suprarenal (above renal arteries) and infrarenal (below renal arteries) aortic infusions of nociceptin were similar to intravenous infusion (See FIG. 6). Together these data suggest nociceptin acts on a non-renal site to induce increases in urinary flow rate. These data are consistent with data published by Kapusta et al.(17) demonstrating that nociceptin acts directly on a site in the central nervous system to induce a diuretic, antinatriuretic response in vivo.

EXAMPLE 5
EFFECTS OF LOWER DOSES OF NOCICEPTIN

Data showing the effects of nociceptin on renal function are illustrated in FIG. 7. Intravenous infusion of nocicepin into conscious rats produced a dose-dependent increase in urine flow rate (V). These renal responses were slow in onset, had a peak effect 30 min. after the start of the nocicepin infusion, and lasted approximately 90 min. These infusion rates of nociceptin did not alter baseline systemic arterial pressure and heart rate. These marked increases in urine flow rate occurred at doses approximately 120 fold lower than previously reported by Kapusta et al. (17). In order to confirm these more recent and complete studies of the present invention, nociceptin was obtained from three commercially available sources, Phoenix Pharmaceutical, Bachem Chemical and Peninsula Laboratories. A total of thirty six rats were divided into six groups and were used to investigate the effects of intravenous (i.v.) infusion rates (50 and 166 nanog/Kg/min) of nociceptin on renal function. Nociceptin from each of the sources above was studied at a single infusion rate in each group of six rats. Since the renal effects of nociceptin obtained from the three different commercial sources were similar and not statistically different, only a single gorup at each dose is presented (see FIG. 7). These increases in urine flow were accompanied by a decrease in the excretion of urinary sodium ($U_{NA}V$) as reported earlier (17). These more current and more extensive experiments of the instant application suggest nociceptin has greater (more potent) diuretic activity than originally reported by Kapusta et al (17).

EXAMPLE 6
MECHANISM OF ACTION OF NOCICEPTIN

As shown in FIG. 4A, i.c.v. injection of dynorphin A (10 μg) produced a similar peak increase in urine flow rate and decrease in urinary sodium excretion as compared to that elicited by i.c.v. nociceptin (10 μg nociceptin data from FIG. 1 superimposed in FIG. 4A). Despite these similar excretory patterns, the onset of diuresis produced by nociceptin was significantly delayed (p<0.05 at time 20 min) (FIG. 4A). In separate animals (FIG. 4B), i.c.v. pretreatment with the selective kappa-opioid receptor antagonist, nor binaltorphimine, completely prevented the diuresis and antinatriuresis produced by dynorphin A. This finding is consistent with the notion that kappa-opioid agonist invariably produce a diuretic (and antinatriuretic) response by a pathway that involves activation of kappa-opioid receptors (4, 8). In contrast, i.c.v. pretreatment with norbinaltorphimine did not alter the diuretic or antinatriuretic response elicited by central nociceptin (FIG. 4B). Together, these results clearly demonstrate that nociceptin affects the renal handling of water and sodium by a central pathway independent of kappa-opioid receptors.

Administration of L-nitro arginine methyl ester (L-NAME), a known inhibitor of constitutive nitric oxide synthase (cNOS), forty-five minutes prior to the initiation of the nociceptin infusion significantly inhibited the increase in urine flow rate (V) in response to i.v. infusion of nociceptin (See, FIG. 8). This dose of L-NAME (30 mg/Kg i.v.) did not alter baseline urine flow rate (V). Since L-NAME did not alter urine flow rate (V) in response to furosemide (Lasix™), a loop diuretic, the present data suggest L-NAME acted in a selective manner to inhibit the renal repsonses to nociceptin (See FIG. 9). Moreover, the present data suggest the increase in urinary flow rate (V) in response to nociceptin depends on the formation of nitric oxide by cNOS.

Additional data of the instant invention demonstrate the aortic vasorelaxant response to nociceptin in vitro and the systemic vasodilator response to nociceptin in vivo are blocked by a variety of inhibitors of nitric oxide formation and nitric oxide function including endothelial cell removal, methylene blue, L-NAME and L-$N^5$-(1-imino ethyl) ornithine (L-NIO). (See FIGS. 10–12). The lack of an inhibitory effect by cycloxygenase blockade following administration of meclofenamate confirms that vasodilator prostaglandins and prostacyclin do not mediate the vasorelaxant response to nociceptin (See FIG. 12).

Male rats (250–350g) were anesthetized with pentobarbital sodium (30 mg/Kg i.p). The rat lungs were quickly removed and immersed in cold (4° C.) Krebs-Henseleit (K-H) solution (composition mM: NaCl 118, KCl 4.7, $CaCl_2$ 2.5, $KH_2PO_4$ 1.2, $NaHCO_3$ 25, $MgSO_4$ 1.2, and dextrose 10). Pulmonary arteries (PA) were isolated and excess fat and connective tissue were removed. Vessels were cut into rings of about 2.5–3 mm in length and were mounted in organ baths containing 5 ml K-H solution. Two stainless steel hooks were inserted into the lumen of the pulmonary artery (PA), one was fixed while the other was connected to a transducer. The tissue bath solution was maintained at 37° C. and bubbled with a 95% $O_2$–5%$CO_2$ mixture. The pulmonary arteries were equilibrated for 90 min with three changes of K-H solution and an optimal tension of 1 gr. applied. Contractions were measured isometrically with a force displacement transducer (FTO3, Grass, USA) and were recorded on a Grass model 7 polygraph. The contractile ability of each ring was then examined by exposure to 60 mM KCl, then washed and allowed to dilate to baseline tension. Only when low reproducible contractions could be elicited was the individual ring used in further studies. The integrity of the endothelium was determined by obtaining a maximal vasorelaxant response to ACh. The concentrations of all drugs were reported as the final molar concentration (M) in organ chambers.

The effects of inhibitors of nitric oxide formation on the systemic vasodepressor response to bolus intravenous (i.v.) injections of nociceptin were also studied in vivo (See FIGS. 13 and 14). Male rats (250–300 g) were anesthetized with pentobarbital sodium (30 mg/kg i.p.). Catheters were placed into a femoral artery and femoral vein for measurement of systemic atrial blood pressure and administration of drugs, respectively. Cardiac output was calculated by using Columbus 2F thermodilution catheter placed fluoroscopically in the ascending aortic arch assess changes in temperature following a thermal reference injection of saline (0.2 ml) at room temperature into the right atrium via a jugular venous catheter. Changes in systemic arterial pressure were measured using a Gould P23Id pressure transducer and recorded on a Grass Model 7A recorder. Cardiac output was determined using a Columbus Cardiomax thermodilution cardiac output computer. Bolus intravenous (i.v.) injections of nociceptin decreased systemic arterial pressure in a dose-dependant manner. Forty-five minutes following administration of L-NAME or L-NIO, the systemic vasodepressor response to nociceptin in vivo was significantly inhibited. The dose-dependent reductions in systemic arterial blood pressure in response to nociceptin reflected reductions in systemic vascular resistance since these doses of nociceptin i.v. did not significantly alter cardiac output (See Table 1).

TABLE 1

Hemodynamic responses to intravenous (i.v.) bolus injection of Nociceptin in the systemic vascular bed of the anesthetized rat.

|  | Systemic Arterial Pressure (mmHg) | Cardiac Output (ml/min) | Systemic Vascular Resistance (mmHg/ml/min) |
| --- | --- | --- | --- |
| Baseline | 169.0 +/− 16.6 | 96.5 +/− 22.5 | 1.7 +/− 0.2 |
| 0.3 ug, i.v. | *150.0 +/− 15.5 | 111.3 +/− 49.6 | *1.1 +/− 0.1 |
| Baseline | 170.0 +/− 25.9 | 96.8 +/− 21.4 | 1.8 +/− 0.3 |
| 1.0 ug, i.v. | *141.0 +/− 17.8 | 102.8 +/− 4.5 | *1.1 +/− 0.2 |
| Baseline | 159.2 +/− 25.0 | 103.6 +/− 28.3 | 1.5 +/− 0.2 |
| 3.0 ug, i.v. | *109.6 +/− 19.8 | 96.8 +/− 34.4 | *0.8 +/− 0.1 |

Values are means +/−SE; N=6. *p,0.05 compared with corresponding control (paired t test).

Recently, data showing that nociceptin decreases systemic arterial pressure in the rate through a naloxone-insensitive manner are consistent with the results in this application demonstrating nociceptin acts on a non-opioid, distinct receptor to dilate the systemic circulation (18).

Figure 15B:
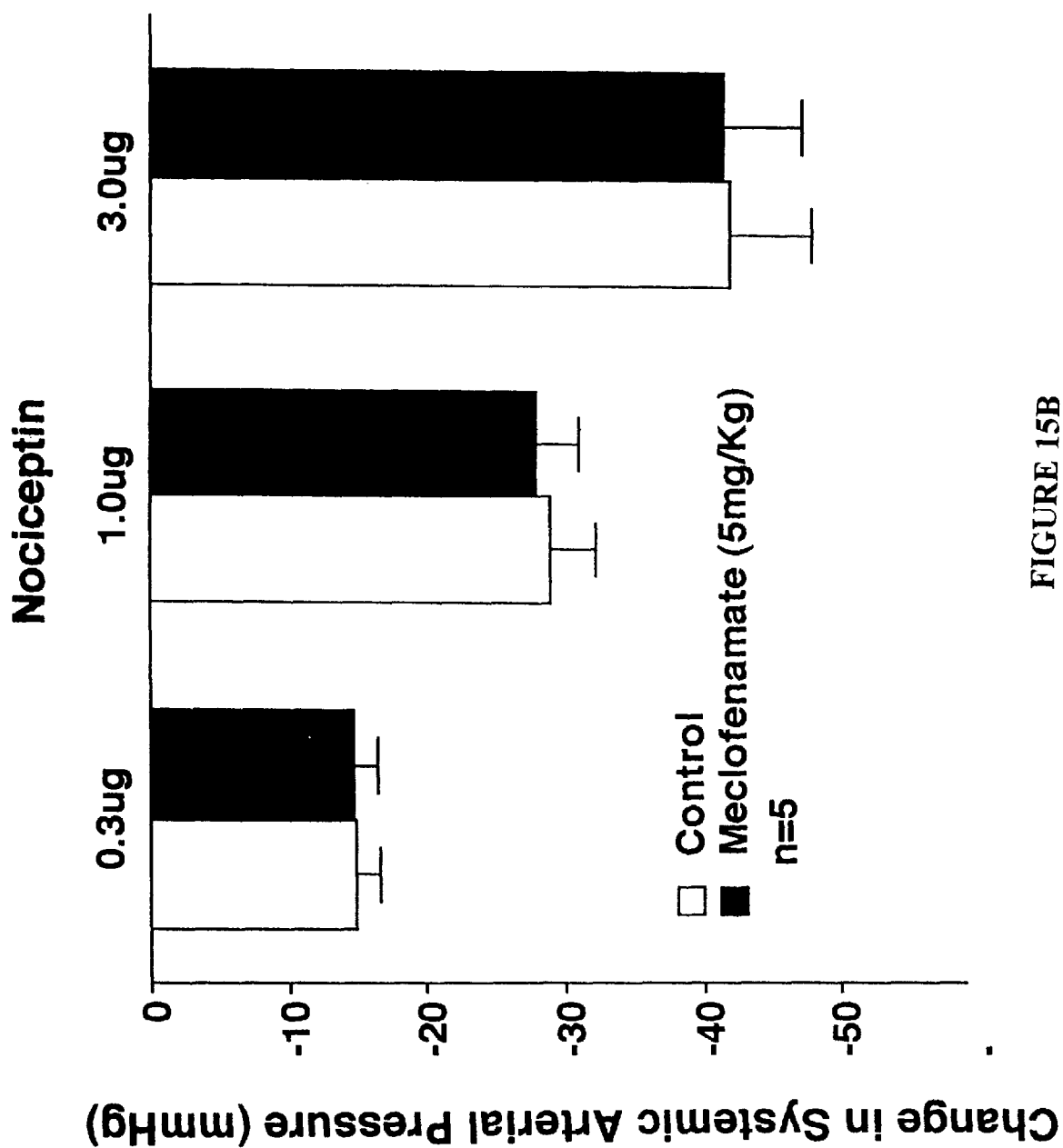

Pharmacologic confirmation that the biologic properties of nociceptin depend on the release of nitric oxide was obtained from studies using glybenclamide and meclofenamate (See FIG. 15). Since the bolus intravenous (i.v.) injections of nociceptin were not inhibited by glybenclamide (See FIG. 15A) and meclofenamate (See FIG. 15B), the present data indicate the systemic vasodilator response to nociceptin is dependent on the release of nitric oxide and independent of activation of ATP-dependent potassium channels and the formation of cyclooxygenase products including prostacyclin.

Taken together, the above vascular and renal data of the instant invention suggest the nociceptin receptor is coupled to cNOS activity and that both the vascular and renal responses to nociceptin depend on the formation of nitric oxide.

EXAMPLE 7
DIVERGENT INFLUENCE OF ANESTHESIA ON THE RENAL AND VASCULAR EFFECTS OF NOCICEPTIN

In order to determine the effects of anesthesia on the increases in urinary flow rate (V) in response to nociceptin, additional studies were performed in conscious and pentobarbitol-treated rats. The ability of nociceptin to increase urinary flow rate (V) was inhibited in rats anesthetized with sodium pentobarbital (See FIG. 16). These data suggest that nociceptin would be expected to retain full diuretic activity in the conscious state as desired for potential clinical use. The relative activity of nociceptin as a vasodilator substance is reversed in the anesthetized state when compared to the conscious state (see FIG. 17). Bolus i.v. injection of nocicpetin had greater systemic vasodepressor activity in anesthetized rats when compared to conscious rats (See FIG. 17). These data suggest that the diurectic and vasodilator activity are differentially influenced by anesthesia and such a profile of response to a nociceptin receptor agonist would be desireable as a clinical diuretic. Based on the studies presented in the instant invention., the therapeutic window for diuresis would be expected to be wider than originally anticipated (17) since concurrent and untoward systemic hypotension does not occur for a large dose-range for nociceptin-induced diuresis in the conscious state.

EXAMPLE 8
DIRECT RENAL AND PULMONARY ACTIONS OF NOCICEPTIN

Additional studies were performed in vitro to determine the contribution of changes in regional hemodynamics in the systemic vasodilator response to nociceptin. Additional data demonstrate nociceptin possesses the ability to relax isolated feline renal (See FIG. 18), femoral, mesenteric and carotid arterial rings (with endothelium) precontracted with phenylephrine (19).

Based on in vitro and in vivo studies in the rat and cat above, it is possible that similar to other renal vasorelaxant substances, nociceptin may induce a diuretic response by increasing renal blood flow. However, in all experiments mentioned in this application investigating the effects of nociceptin on urine flow rate (V), the dose of nociceptin studied was below the dose necessary to alter systemic and regional hemodynamics. Therefore, alterations in renal blood flow and the vasodilator properties of nociceptin contribute little, if any, to the diuretic activity of nociceptin as presented in this application.

In its potential clinical use as a diuretic nociceptin agonist could be delivered intravenously, topically such as patch or paste form, orally, or inhaled similar to an aerosolized bronchodilator substance. In order to access nociceptin's active site in the central nervous system using these known mechanisms of delivery, a nociceptin agonist will necessarily traverse the pulmonary circulation. Therefore, additional studies were performed to determine the actions of nociceptin in the pulmonary vasular bed and to determine the ability of first-pass lung transit to influence the biologic properties of nociceptin.

Male Charles River rats (260–340 go) were anesthetized with an intraperitoneal injection of pentobarbital sodium (30 mg/kg), and allowed to breath air enriched with oxygen through an endotracheal tube inserted by tracheotomy. The anesthetized animals were strapped in a supine position to a fluoroscopic table, and catheters were inserted in femoral blood vessels. A specially designed triple lumen balloon perfusion catheter was constructed (Nu-Med, Hopkinton, N.Y.). This catheter is 145 mm in length, 1.1 in O.D. and with specially curved tip to facilitate passage through the right heart and main pulmonary artery into the artery supplying the right lower lung lobe. At the distal tip of the catheter is a pressure port through which a 0.25 mm soft tip coronary artery angioplasty guide wire is inserted. Two mm proximal to this port if a perfusion port which permits easy passage of an 0.34 mm soft-tipped coronary guide wire. A plastic non-dispensable balloon is affixed to a third port just proximal to the perfusion port. When fully distended with contrast material, the balloon is 4.0 mm in diameter and 3.5 mm in length. Before introduction, this catheter curve is initially straightened wire with 0.45 mm straight wire in the pressure port to facilitate passage from the right jugular vein into the right atrium at the tricuspid valve. As the straight wire is removed, the natural curve permits easy entry into the right ventricle. The catheter is then passed over a 0.25 mm soft-tipped guiding catheter to the main pulmonary artery and then into the right lower lobe artery. Mean pressure in the right lower lobe artery and the aorta were continuously recorded. After intravenous injection of Heparin (1000 units/kg), the balloon is then distended with radiopaque material until the lobar arterial pressure falls to pulmonary capillary wedge pressure. The distal portion of the right lower lung lobe was then perfused with blood removed from a carotid artery with an extracorporeal pump (Masterflex Quick-Load Rotary Pump Model #7021-24). The volume of extracorporeal tubing was 1.8 ml. At a perfusion rate of 14.0±0.62 ml/min, pressure in the perfused lobar artery approximated that in the main pulmonary artery, and this perfusion rate was taken as control blood flow. Since this catheter perfuses approximately one-sixth of the lung, as determined by measuring lung weight, this perfusion rate approximate physiologic flow for that lung area, i.e. at least 15–20% of the 75–85 ml/min normal total pulmonary blood flow of the rat. After cardiac catheterization was completed and constant pulmonary blood flow was established in the right lower lung lobe, pulmonary vasomotor tone was raised by a continuous intralobar arterial infusion of U46619, a thromboxane $A_2$ mimic, (1.5–2.5 $\mu$g.min). After pressures were stabilized, the intralobar arterial bolus injections of testing agents were given.

Since bolus injections of nociceptin into the right atrium and into the left atrium of intact-chest, anesthetized rats produced similar reductions in systemic arterial pressure (See FIG. 19 ), the present data suggest nociceptin does not undergo significant first-pass uptake or metabolism in the lung. The present data also suggest the lung does not release a vasodilator substance that contributes in large measure to the systemic vasodilator response to nociceptin. Moreover, clinical delivery of nociceptin to the central nervous system to induce diuresis would not be expected to be influenced by lung transit. In addition, nociceptin would not be expected to be detrimental to the pulmonary circulation since nociceptin dilates the pulmonary vascular bed similar to the systemic vasular bed (See FIG. 20). Such a hemodynamic profile would be particularly desireable in patients experiencing congestive heart failure since pulmonary vasodilation would be expected to enhance resolution of pulmonary edema and systemic vasodilation (i.e. afterload reduction) would be expected to enhance myocardial performance.

Since L-NAME and L-NIO also inhibit the pulmonary vasodilator response to nociceptin (See FIG. 21), the present data indicate the renal and vascular responses to nociceptin including the pulmonary, systemic and regional vasodilator responses to nociceptin are all mediated by the release of nitric oxide formed by cNOS.

In general, a nociceptin receptor agonist would be expected to be a desireable therapeutic alternative to many clinically used diuretics including furosemide (Lasix™) since diuresis from nociceptin receptor activation does not cause urinary loss of electrolytes and potential acid base disorders.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

REFERENCES

1. E. J. Simon and T. L. Gioannini, in *Opioids I*, A. Herz, Ed., Springer-Verlag, New York (1993), pp. 1–26.
2. C. Mollereau et al, *FEBS Lett*. 341, 33 (1994).
3. J. R. Bunzow et al., *FEBS Lett*. 347, 284 (1994); J. B. Wang et al., *FFBS Lett*. 348, 75 (1994); K. Funkuda et al, *FEBS Lett*. 343, 42 (1994); Y. Chen et al., *FEBS Lett*. 347, 279 (1994); M. J. Wick et al., *Mol. Brain Res*. 27, 37 (1994); J. E. Lachowicz et al., J. Neurochem. 64, 34 (1994); W. P. Halford et al, *J Neurochem*. 59, 91(1995).
4. J. C. Meunier et al., *Nature*, 377, 532 (1995).
5. R. K. Reinscheid et al., *Science*, 270, 792 (1995).
6. J. W. Holaday, *Ann. Rev. Pharmacol Physiol.*, 22, 891 (1995).
7. D. R. Kapusta, *Clin. Exp. Pharmacol. Physiol.*, 22, 891 (1995).
8. G. R. Slizgi, C. J. Taylor, J. H. Ludens, *J. Pharmacol. Exp. Therap.*, 230, 641 (1984); J. D. Leander, *J Pharmacol Exp. Therap.*, 224, 89 (1983); S. P. Salas, et al, *J Pharmacol. Exp. Therap.*, 250, 992 (1989); D. R. Kapusta, S. Y. Jones, G. F. Dibona, *Pharmacol. Exp. Therap.* 251, 230 (1989); S. P. Salas et al., *J Pharmacol. Exp. Therap.*, 262, 979 (1992); D. R. Kapusta and J. C. Obih, *J Pharmacol, Exp. Therap.*, 267, 197 (1993); Y. X. Wang et al., *J. Pharmacol Exp. Therap.*, 270, 244 (1994).
9. D. R. Kapusta, S. Y. Jones, G. F. DiBona, *J Pharmacol Exp. Therap.* 251, 230 (1989).
10. D. Julius, *Nature*, 377, 476 (1995); P. M. Rowe, Lancet, 347, 606 (1996).
11. D. R. Kapusta and J. C. Obih, *J. Pharmacol. Exp. Therap.*, 267, 197 (1993).
12. P. A. Reece et al., *J Clin. Pharmacol*. 34, 1126 (1994).
13. A. Pfeiffer et al, *Science*, 233, 774 (1986),
14. Y. Shimohigashi et al, *The Journal of Biological Chemistry*, 271(39), 23642 (1996).
15. L. Stryer, in Biochemistry, L. Stryer, Ed., W. H. freeman and Company, New York (1988), pp. 178, 268–269, 994–995.
16. J. Yu, et al, *Peptides* 17(5), 873, 1996.
17. D. Kapusta et al., Life Sciences 60:PL 15–21, 1997.
18. H. C. Champion and P. J. Kadowitz, *Biochem. and Biophys Res. Comm.*, 234, 309–312 (1997).
19. B. Gumuse et al, Life Sciences, 60:PL141–145, 1997.

What is claimed is:

1. A method for producing free-water diuresis in a patient in need of free-water diuresis, which comprises administering to a patient a therapeutically effective amount of nociceptin.

2. The method of claim 1, wherein the nociceptin produces a free-water diuresis.

3. The method of claim 1, wherein the patient is suffering from a disease involving a water-balance problem.

4. The method of claim 3, wherein the disease is selected from the group consisting of the syndrome of inappropriate secretion of antidiuretic hormone, congestive heart failure, liver cirrhosis with ascites, hyponatremia, acute and chronic renal failure, nephrotic syndrome, and adult respiratory distress syndrome.

5. The method of claim 1, wherein administration is by intravenous infusion.

6. The method of claim 1, wherein administration is by intracerebroventricular microinjection.

7. The method of claim 2, wherein the free-water diuresis is independent of kappa-opioid receptors.

8. The method of claim 1, wherein administration is via the skin.

9. The method of claim 1, wherein administration is intranasally.

10. The method of claim 1, wherein administration is oral.

* * * * *